(12) United States Patent
Markle et al.

(10) Patent No.: US 10,744,274 B2
(45) Date of Patent: Aug. 18, 2020

(54) RECTAL INJECTION DEVICE AND METHOD OF OPERATION THEREOF

(71) Applicant: Logan Medical Devices, Inc., Dallas, TX (US)

(72) Inventors: Tyler S. Markle, Dallas, TX (US);
Dennis I. Robbins, Dallas, TX (US);
Jose Rodriguez, Dallas, TX (US);
David H. Hitt, Dallas, TX (US)

(73) Assignee: Logan Medical Devices, Inc., Dallas, TX (US)

( * ) Notice: Subject to any disclaimer, the term of this patent is extended or adjusted under 35 U.S.C. 154(b) by 309 days.

(21) Appl. No.: 15/947,375

(22) Filed: Apr. 6, 2018

(65) Prior Publication Data
US 2018/0221594 A1    Aug. 9, 2018

Related U.S. Application Data

(62) Division of application No. 15/625,552, filed on Jun. 16, 2017, now Pat. No. 9,987,437.

(60) Provisional application No. 62/350,812, filed on Jun. 16, 2016, provisional application No. 62/408,302, filed on Oct. 14, 2016.

(51) Int. Cl.
| | | |
|---|---|---|
| A61M 5/32 | (2006.01) |
| A61M 5/315 | (2006.01) |
| A61M 5/20 | (2006.01) |
| A61M 25/00 | (2006.01) |
| A61M 31/00 | (2006.01) |
| A61M 25/04 | (2006.01) |

(52) U.S. Cl.
CPC ............ *A61M 5/3295* (2013.01); *A61M 5/20* (2013.01); *A61M 5/315* (2013.01); *A61M 5/3157* (2013.01); *A61M 5/3287* (2013.01); *A61M 25/0084* (2013.01); *A61M 25/0068* (2013.01); *A61M 25/04* (2013.01); *A61M 31/00* (2013.01); *A61M 2025/0085* (2013.01); *A61M 2025/0086* (2013.01); *A61M 2025/0087* (2013.01); *A61M 2202/04* (2013.01); *A61M 2210/1042* (2013.01)

(58) Field of Classification Search
CPC ...... A61M 2202/04; A61M 2210/1042; A61M 5/20; A61M 5/315; A61M 5/3157; A61M 5/3287; A61M 5/3295; A61M 25/0084; A61M 31/00; A61M 2025/0085; A61M 25/0068; A61M 2025/0087; A61M 2025/0086; A61M 25/04
See application file for complete search history.

(56) References Cited

U.S. PATENT DOCUMENTS

| | | | | |
|---|---|---|---|---|
| 5,304,214 A | * | 4/1994 | DeFord | A61B 18/082 604/916 |
| 5,385,544 A | * | 1/1995 | Edwards | A61B 18/18 604/22 |
| 5,599,294 A | * | 2/1997 | Edwards | A61N 1/40 604/22 |

(Continued)

*Primary Examiner* — Quynh-Nhu H. Vu

(57) ABSTRACT

A rectal injection device and a method of operating a rectal injection device. In one embodiment, the device includes: (1) a handle having a trigger associated therewith, (2) an extension tube extending from the handle and terminating in a head, (3) at least two needles coupled to the head and configured to move relative thereto between a retracted position and a deployed position and (4) a pullrod coupling the trigger and the needles and configured to cause the needles to move.

9 Claims, 46 Drawing Sheets

(56) References Cited

U.S. PATENT DOCUMENTS

| | | | | |
|---|---|---|---|---|
| 5,843,026 | A * | 12/1998 | Edwards | A61B 18/00 604/508 |
| 7,842,011 | B2 * | 11/2010 | Maerten | A61M 25/0084 604/131 |
| 9,561,067 | B2 * | 2/2017 | Sharma | A61B 18/04 |
| 9,629,979 | B2 * | 4/2017 | Gunday | A61B 18/24 |
| 2005/0267414 | A1 * | 12/2005 | Abraham-Fuchs | A61M 31/00 604/173 |
| 2007/0038181 | A1 * | 2/2007 | Melamud | A61B 17/3478 604/158 |
| 2009/0112161 | A1 * | 4/2009 | Maerten | A61M 25/0084 604/131 |
| 2010/0087798 | A1 * | 4/2010 | Adams | A61B 17/320783 604/515 |
| 2011/0270184 | A1 * | 11/2011 | Gunday | A61B 18/24 604/131 |
| 2014/0309486 | A1 * | 10/2014 | Carson | A61K 38/09 600/33 |
| 2016/0144161 | A1 * | 5/2016 | Buysman | A61M 37/0069 604/506 |

* cited by examiner

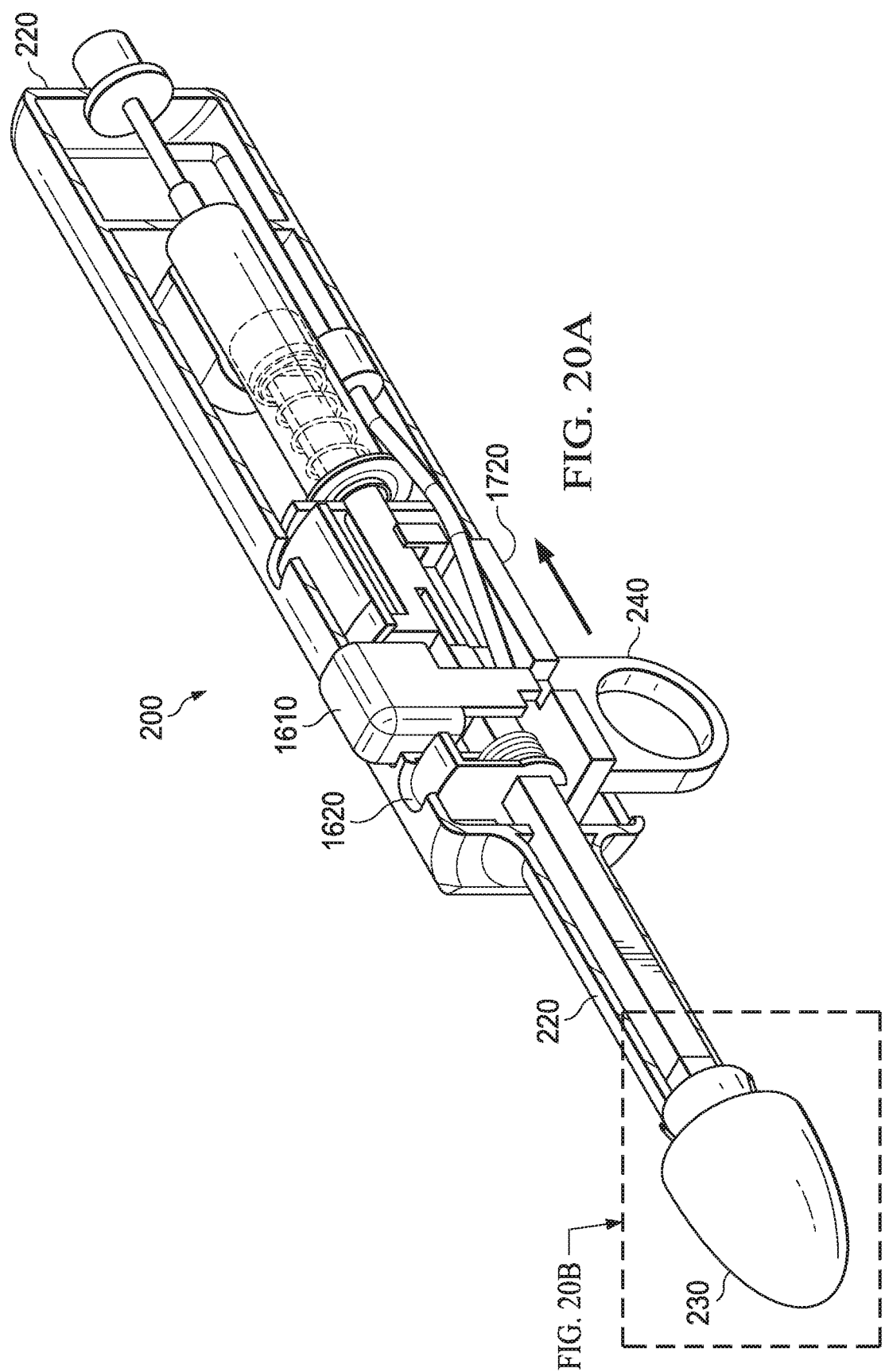

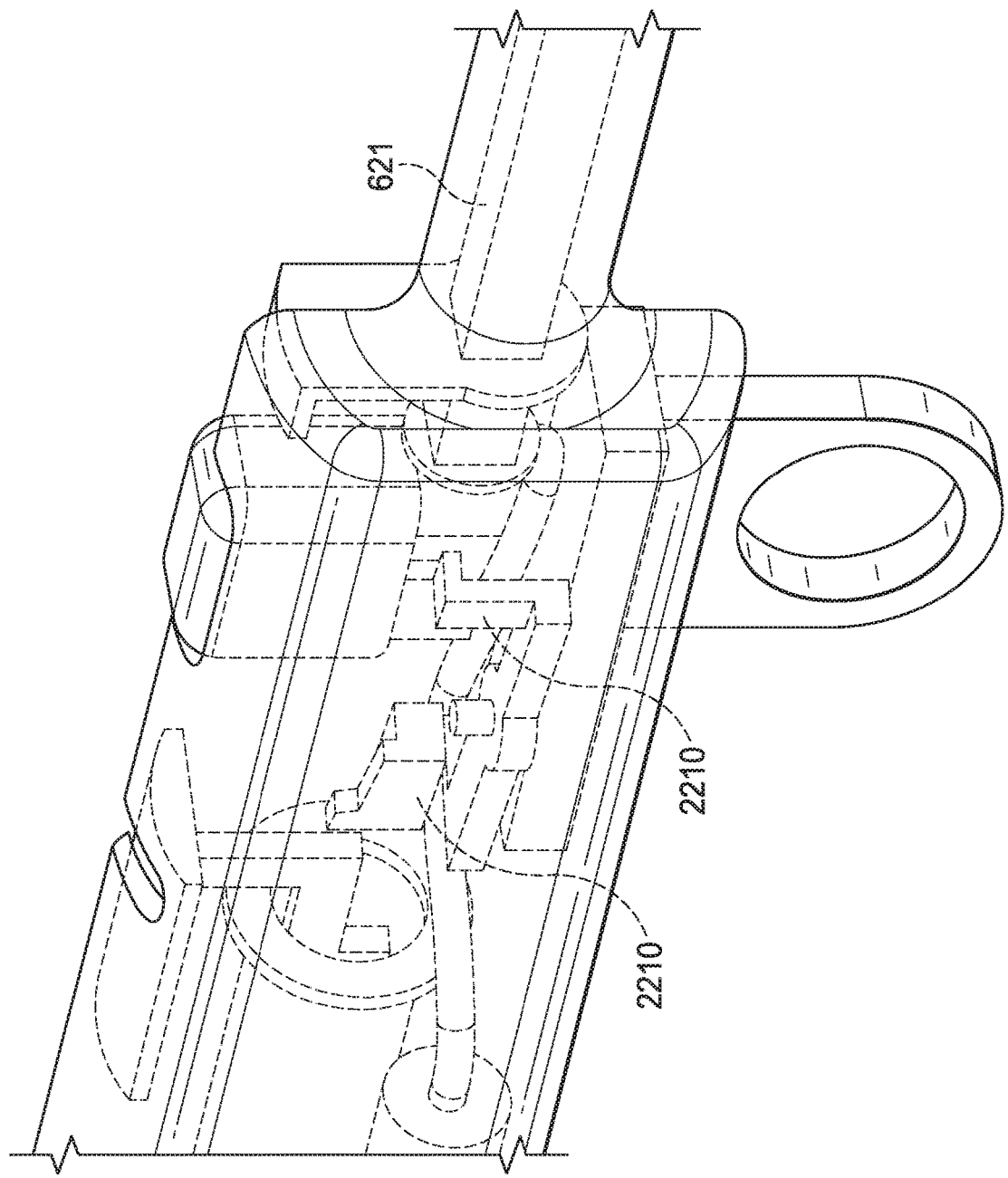

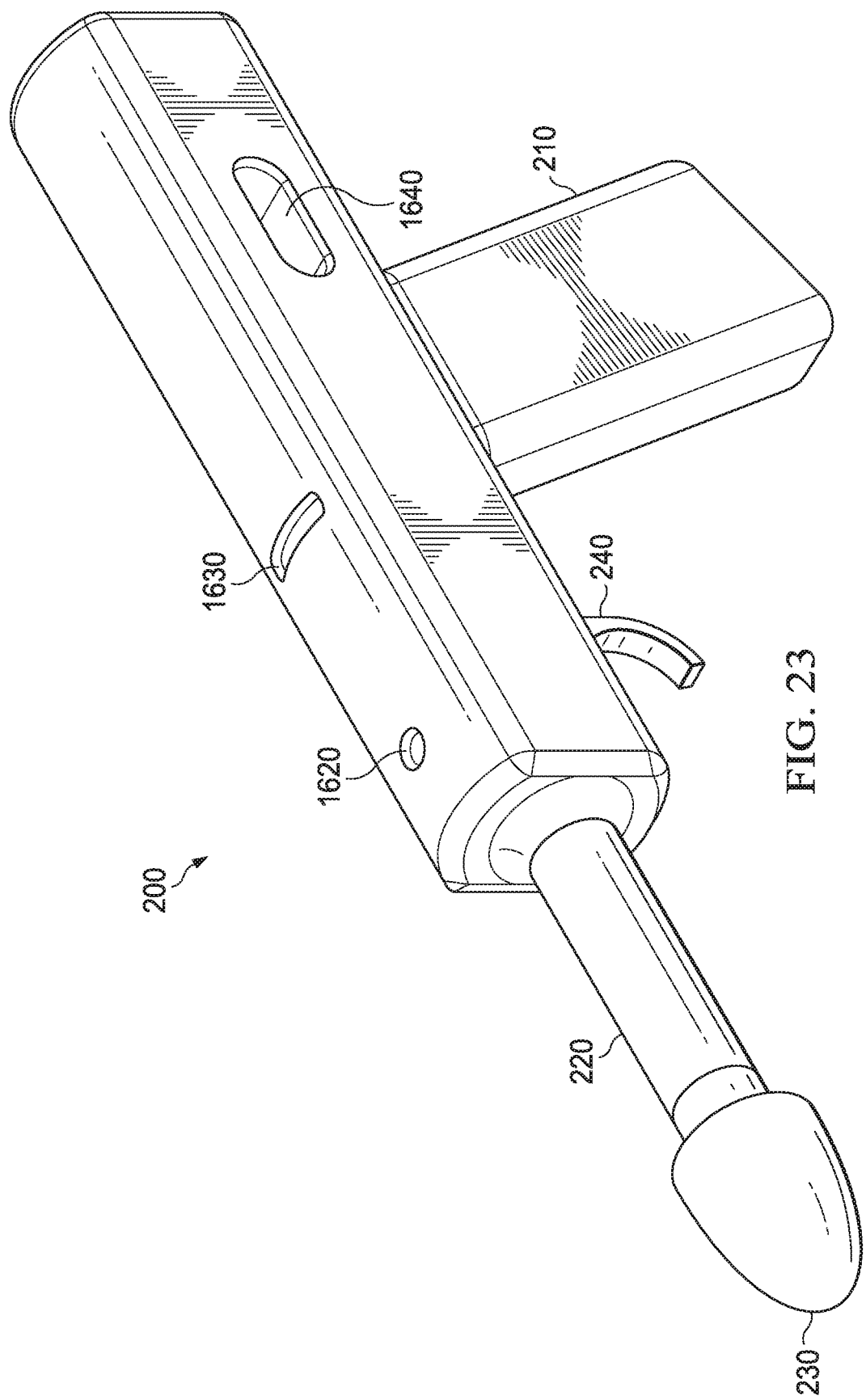

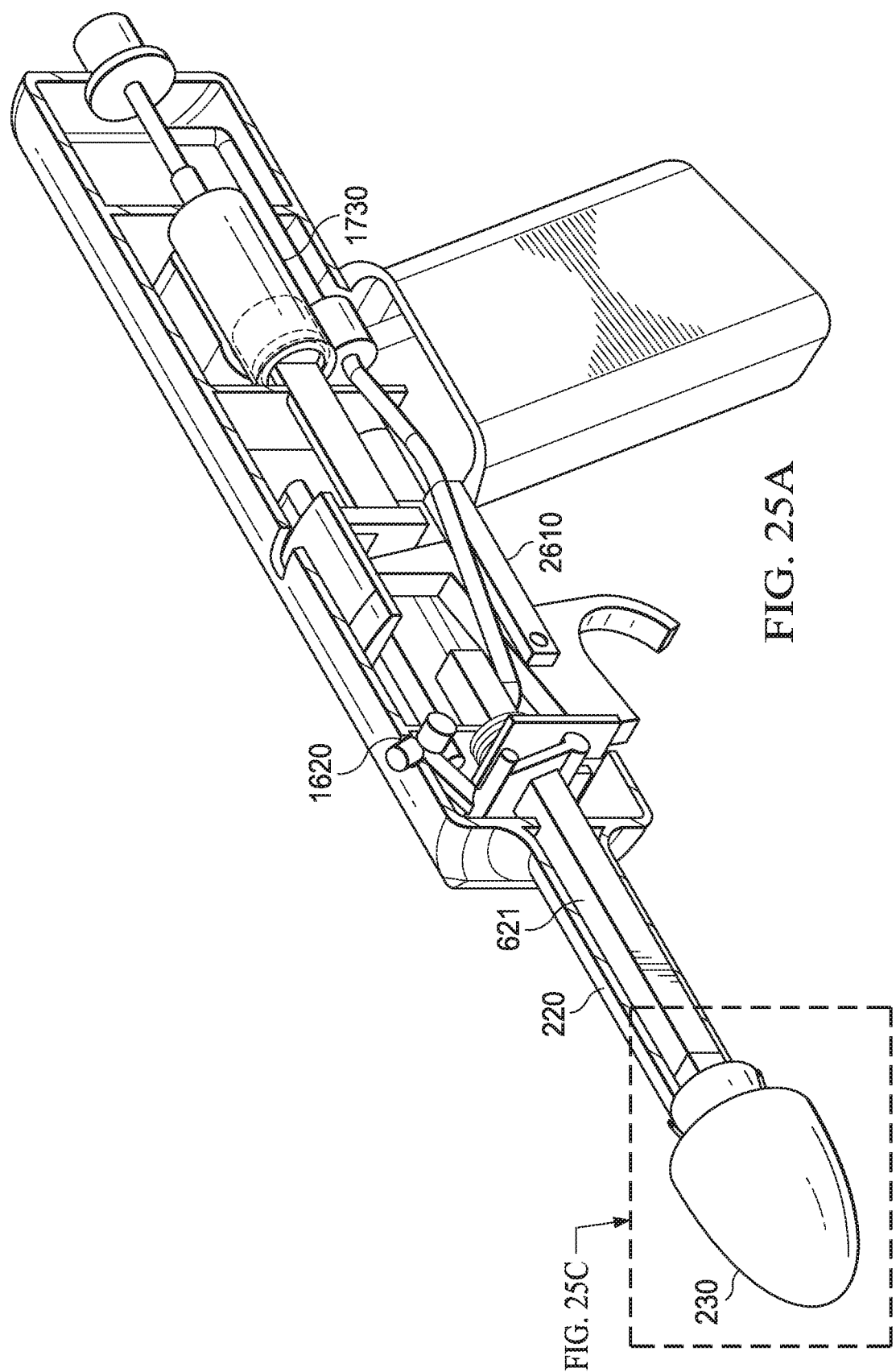

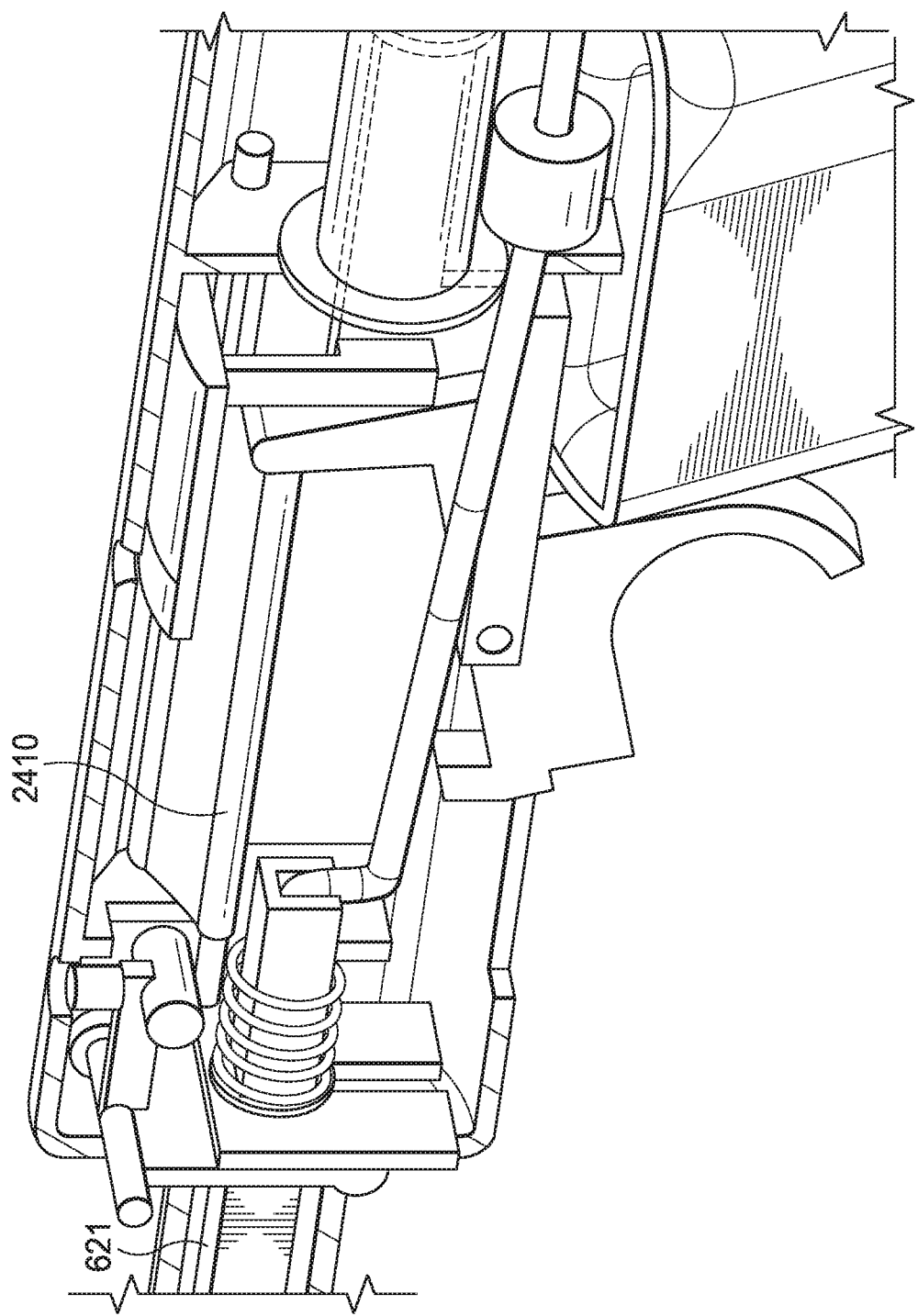

RECTAL INJECTION DEVICE AND METHOD OF OPERATION THEREOF

CROSS-REFERENCE TO RELATED APPLICATIONS

This divisional patent application claims priority to U.S. patent application Ser. No. 15/625,552, filed on Jun. 16, 2017, entitled "Rectal Injection Device and Method of Operation Thereof", and claims priority to U.S. Provisional Patent Application Ser. No. 62/350,812, filed on Jun. 16, 2016, entitled "Rectal Injection Device and Methods of Manufacture and Operation Thereof", and further claims priority to U.S. Provisional Patent Application Ser. No. 62/408,302, filed on Oct. 14, 2016, entitled "Rectal Injection Device and Methods of Manufacture and Operation Thereof". These applications are assigned to the assignee of the present application and are hereby incorporated by reference into the present application as if fully set forth herein.

TECHNICAL FIELD

This application is directed, in general, to an injection device for liquids and, more specifically, to a rectal injection device for liquids and methods of manufacturing and operating the same.

BACKGROUND

Every year hundreds of millions of individuals worldwide suffer from serious lower gastrointestinal (GI) diseases and disorders (e.g., fecal anal incontinence/laxity, hemorrhoids, colitis) requiring intervention. The technology incorporated in the design of gastrointestinal devices has seen little to no developmental progress in recent years. Indeed, biopsy forceps, polypectomy snares and fine aspiration needles have seen so little change that they are becoming commodities. Though these conventional devices remain limited in their efficacy, the incidence of these disease states continues to increase.

Fecal incontinence, the involuntary loss of stool or air per anus, is a common clinical problem, typically resulting from sphincter injury (most often in women during labor). According to the National Health and Nutrition Examination Survey (NHANES) the prevalence of fecal incontinence in U.S. adults is approximately 10%. Nearly 18 million U.S. adults (about 1 in 12) have fecal incontinence. Further, the prevalence approaches nearly 50% of nursing home residents, with no effective non-surgical treatment. Often, fecal incontinence is a primary condition for motivating caregivers to move the elderly into nursing home facilities from private residences. Social embarrassment, fear about the cause, or even a misconception that incontinence is part of the normal aging process may prevent patients from revealing these symptoms to their healthcare providers. The severity of the condition often mandates continuous protection from soiling, and robs patients of their quality of life and independence.

Over $400 million per year is spent on adult diapers and protective clothing in the U.S. alone. These symptoms may persist for years before a patient vocalizes complaints and obtains relief. Adding to this is the financial burden to the individual and society. The healthcare cost of incontinence among U.S. adults in 2000 was estimated at $20 billion. Over 50% of these costs are attributed to resources necessary to manage the patients' condition including nursing home and assisted-living caregiver salaries, and absorbent pads and diapers. The 2010 national annual average cost for fecal incontinence care was $4,000 per person. Treatments for fecal incontinence include fiber supplements, biofeedback to train the sphincter, exercises to tighten the sphincter, and surgery. Unfortunately, these available treatments outside of invasive surgery are lengthy and often ineffective. Inadequate repair or poor healing of obstetric perineal injuries may present as anal incontinence within days to weeks of delivery. In fact, some authors have reported an incidence of anal incontinence after third- or fourth-degree laceration as high as 40-60% of women. Various fillers, such as collagen/silicone, may be injected to treat such laxity by increasing the pressure resistance of the internal sphincter.

Many other GI disorders have a major impact on health. For example, hemorrhoids—inflamed and swollen veins in the anus or lower rectum—are extremely common, accounting for some 50 million procedures performed worldwide. The two most common office-based procedures used to treat symptomatic hemorrhoids are rubber band ligation (RBL) and sclerotherapy (SCL). RBL involves stretching an elastomeric band about a target vein such that it constricts and substantially halts blood flow through the vein, causing it to shrivel over time, thus reducing and eliminating the hemorrhoid. SCL involves injecting a sclerosing solution into a target vein, which causes the vein to shrivel over time, again reducing and eliminating the hemorrhoid.

SUMMARY

One aspect provides a rectal injection device and a method of operating a rectal injection device. In one embodiment, the device includes: (1) a handle having a trigger associated therewith, (2) an extension tube extending from the handle and terminating in a head, (3) at least two needles coupled to the head and configured to move relative thereto between a retracted position and a deployed position and (4) a pullrod coupling the trigger and the needles and configured to cause the needles to move.

In another embodiment, the rectal injection device includes: (1) an elongated handle having a trigger coupled thereto, (2) an internal device syringe located within the handle, (3) an extension tube extending from the handle and terminating in a head configured to seat on an anal dentate of a rectum, (4) at least three needles evenly spaced within the head and configured to move toward the handle from a retracted position to a deployed position, (5) a pullrod coupling the trigger and the needles and configured to cause the needles to move, (6) a needle extension indicator associated with the handle and (7) an injection complete indicator associated with the handle.

Another aspect provides a method of operating a rectal injection device. In one embodiment, the method includes: (1) inserting a head of the device into a rectum of an animal, (2) pulling back the head to cause the head to seat against an anal dentate of the rectum, (3) deploying a plurality of needles of the device from the head so that they enter the rectum proximate the anal dentate and (4) injecting the fluid through the plurality of needles into the anal dentate.

BRIEF DESCRIPTION

Reference is now made to the following descriptions taken in conjunction with the accompanying drawings, in which.

Figure 16:
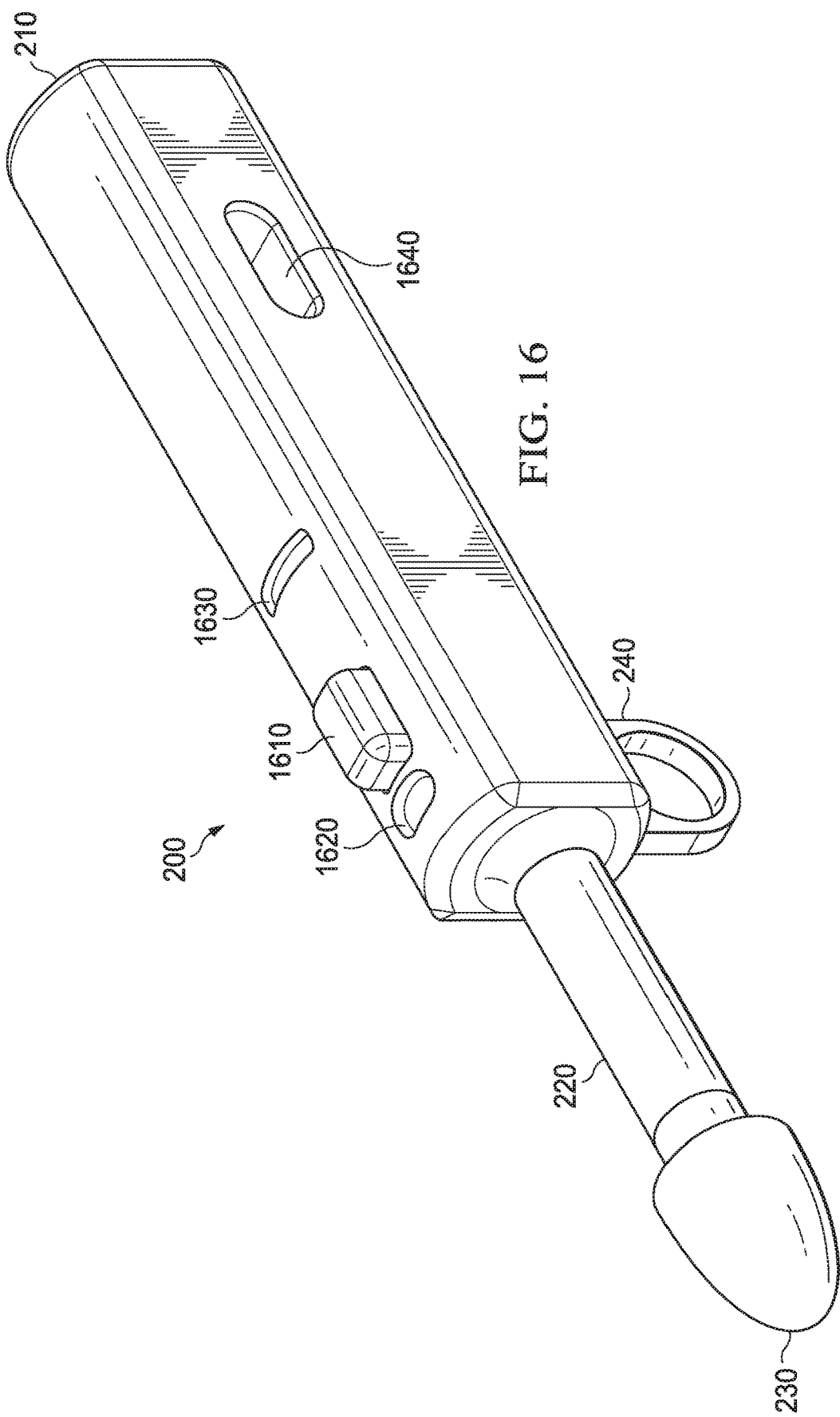
FIG. 16 is an isometric view of a linear embodiment of a rectal injection device.
Figure 18C:
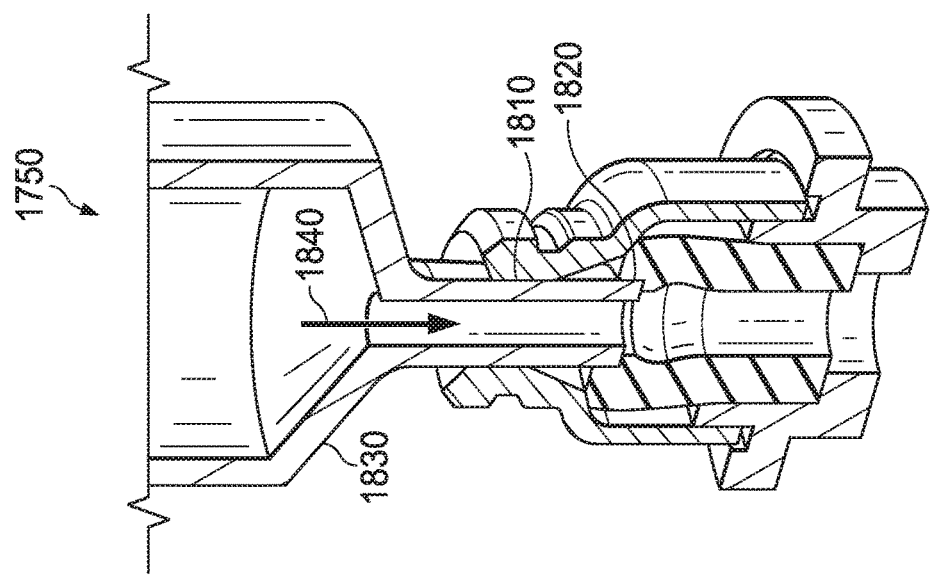
Figure 18B:
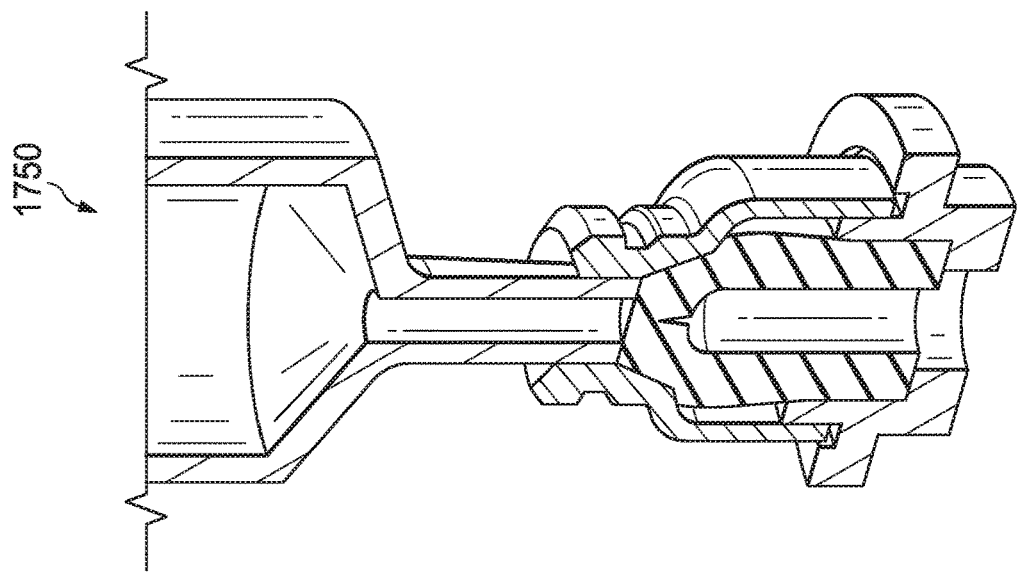
Figure 18A:
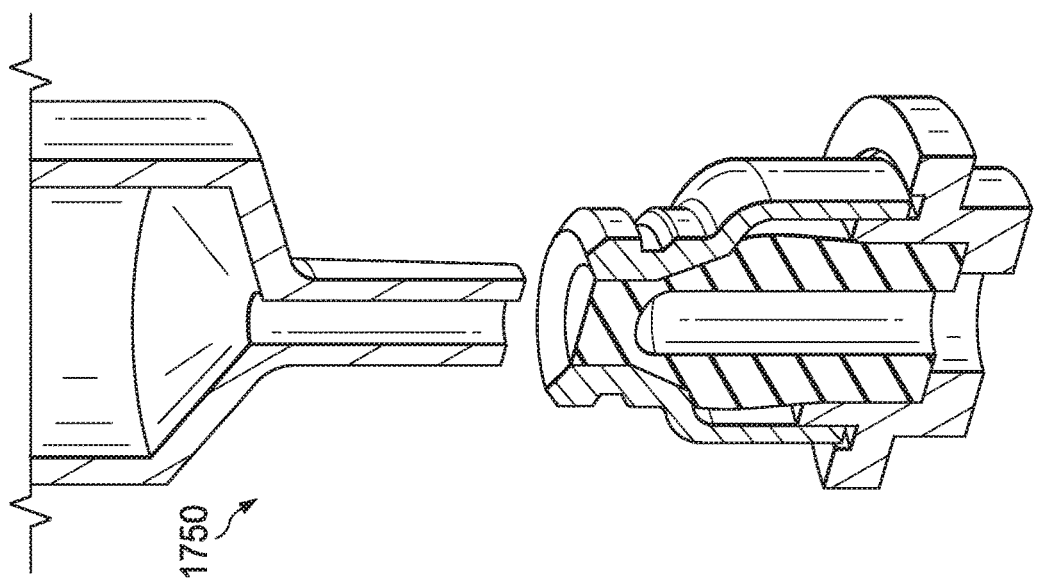
Figure 19A:
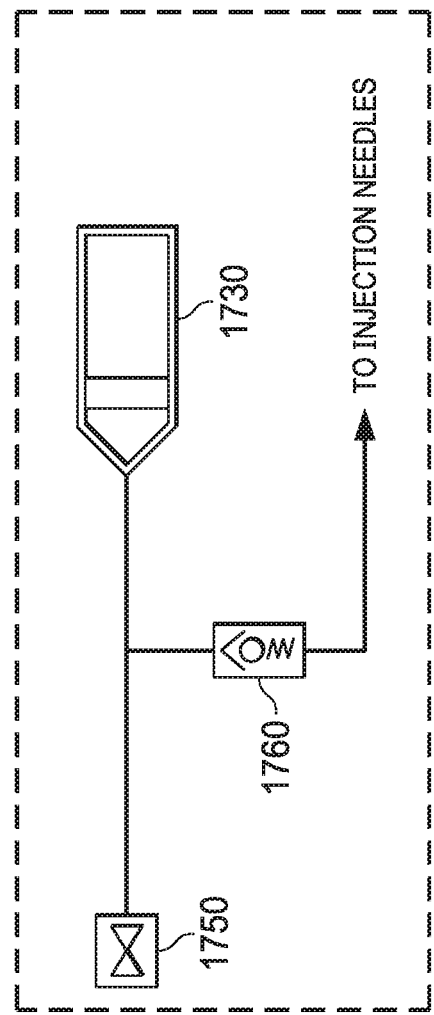
Figure 21A:
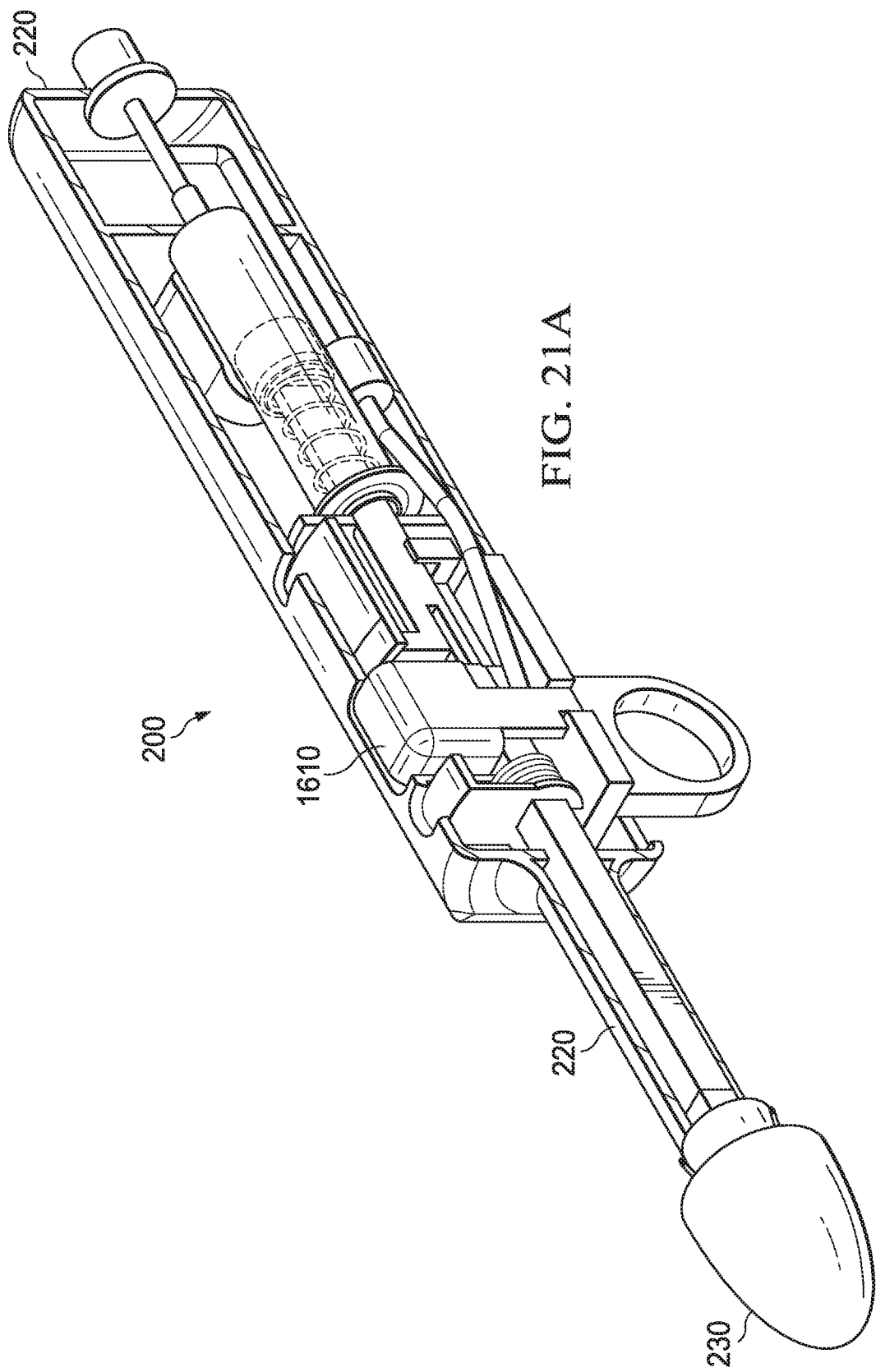
Figure 22A:
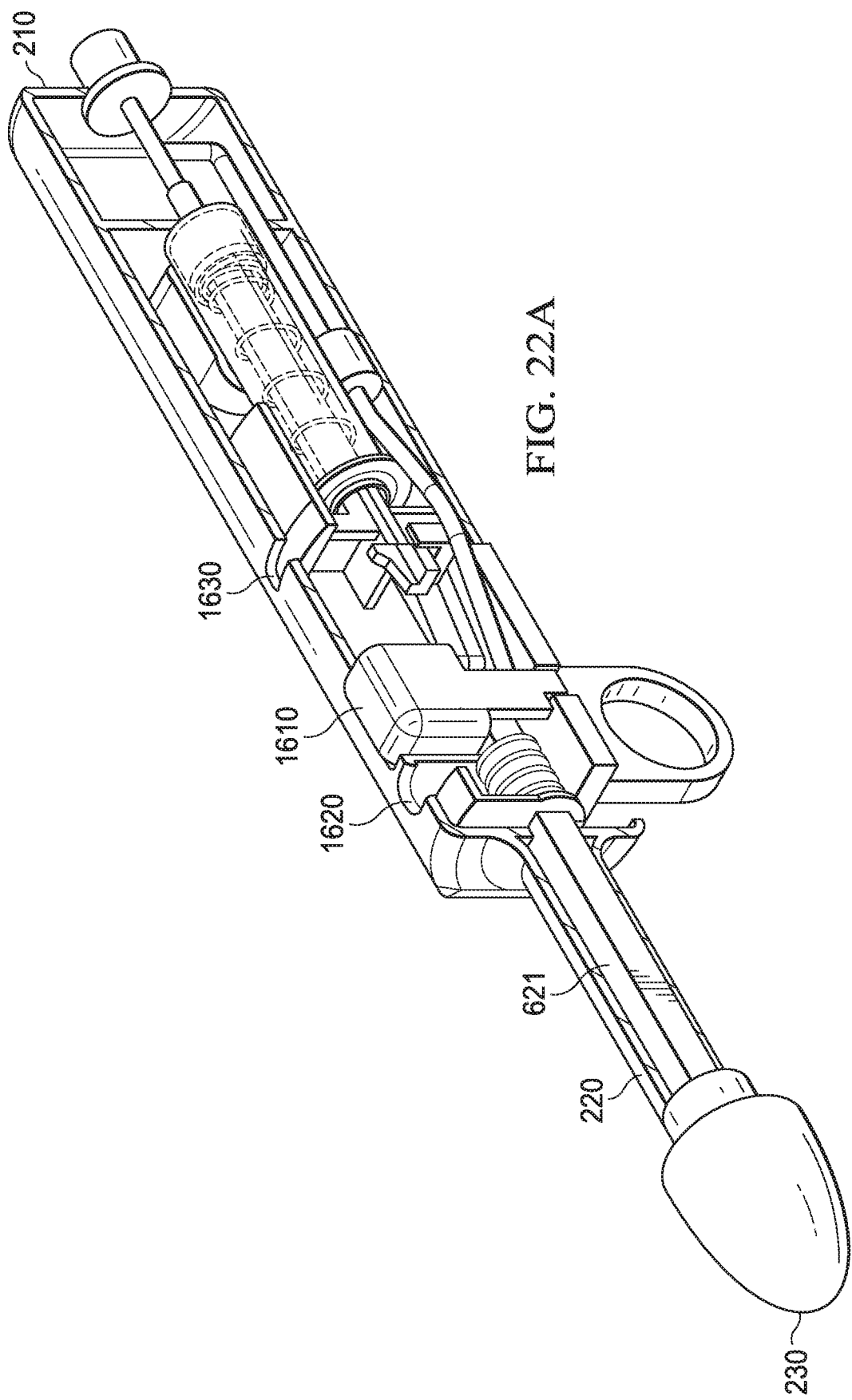
Figure 24:
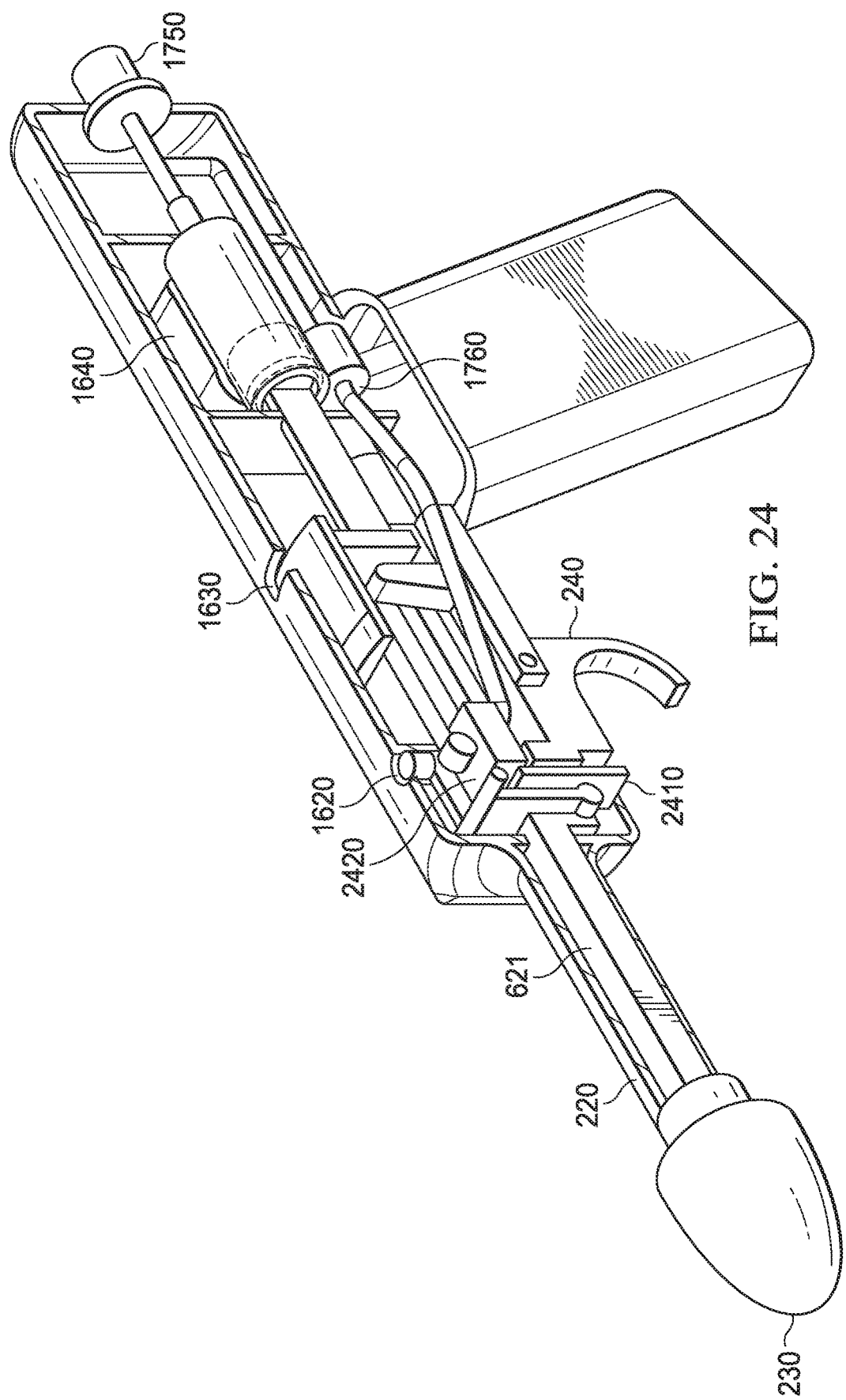
Figure 25B:
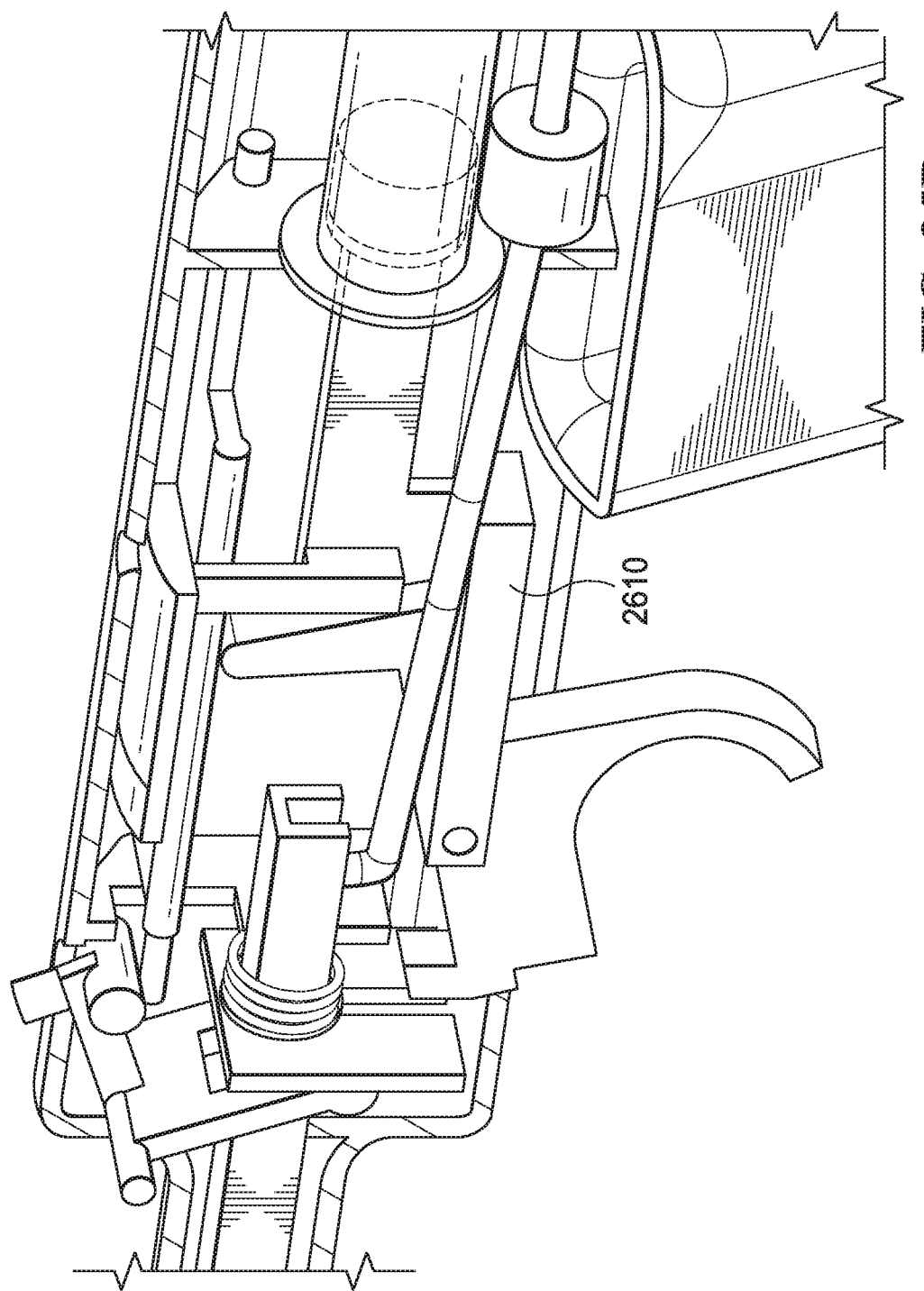
Figure 25C:
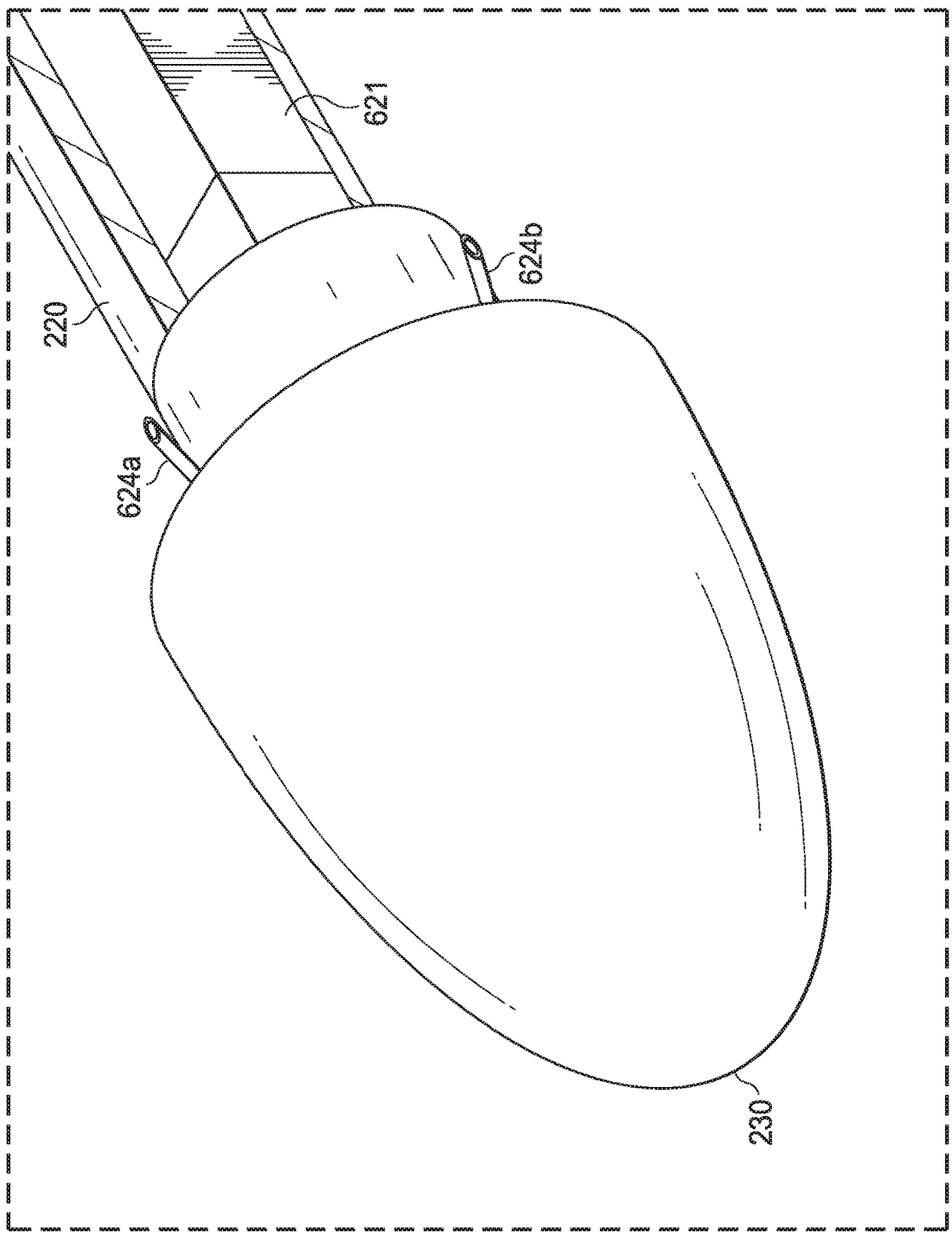
Figure 26:
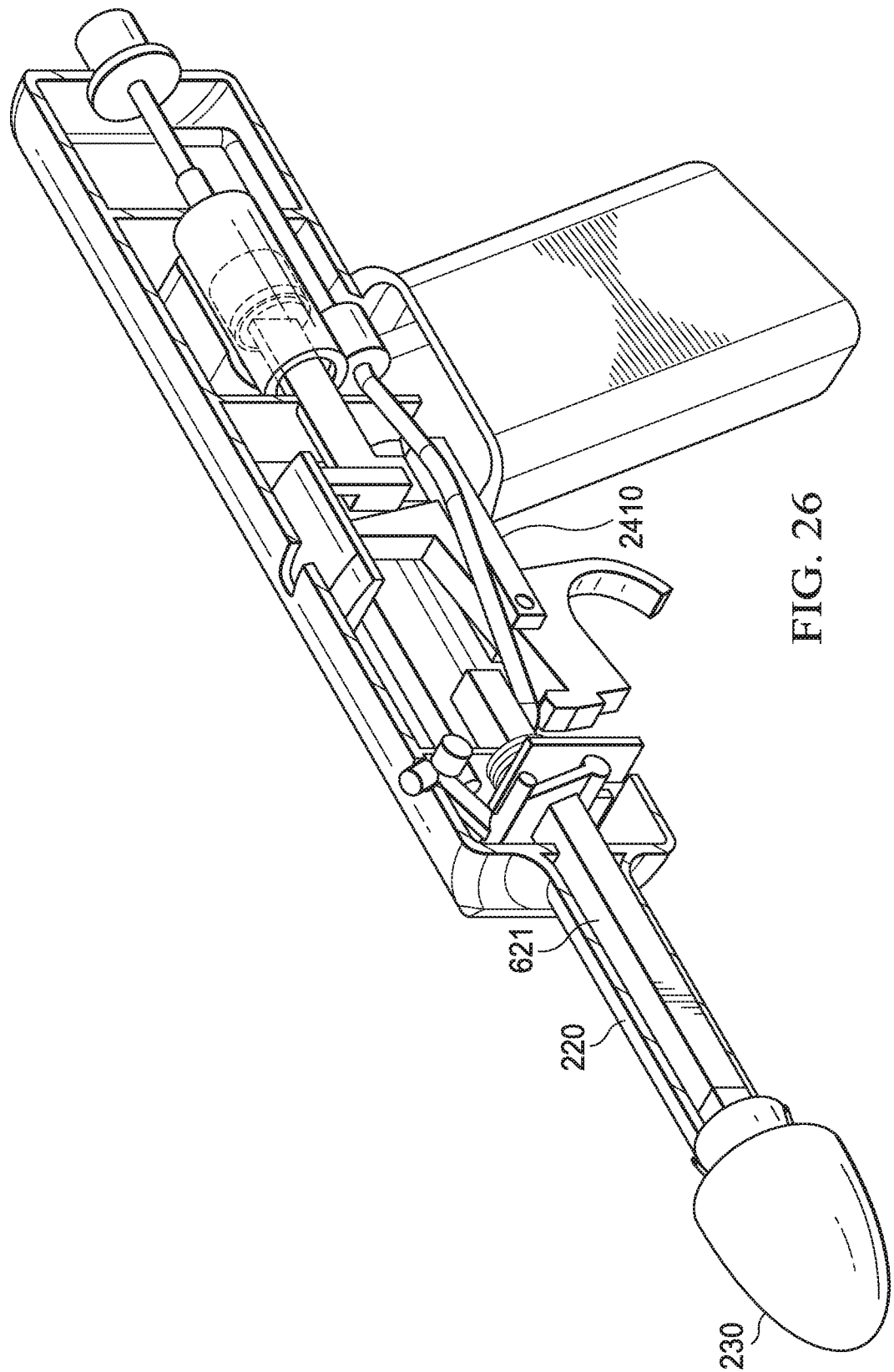
Figure 27A:
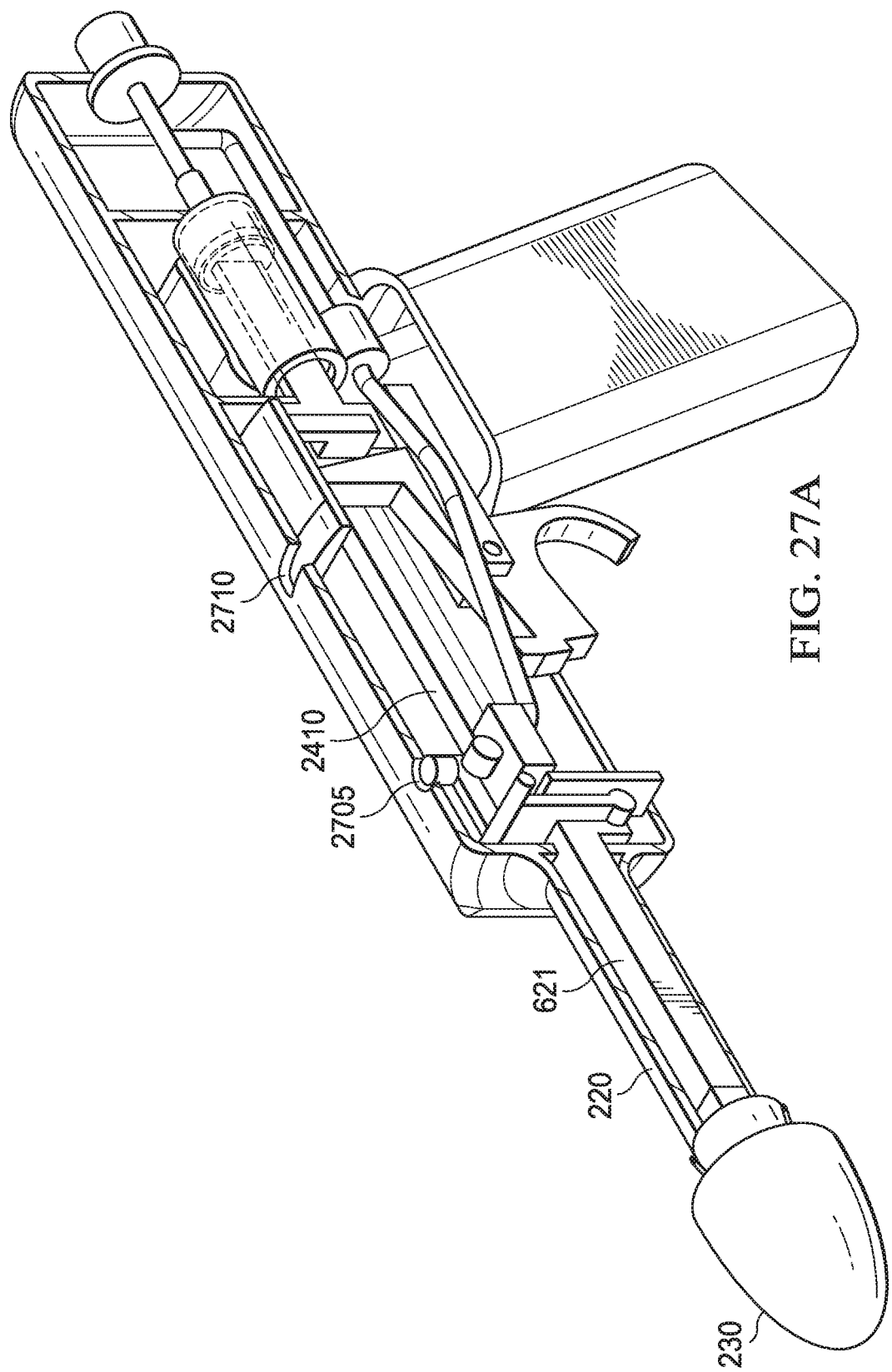
Figure 28:
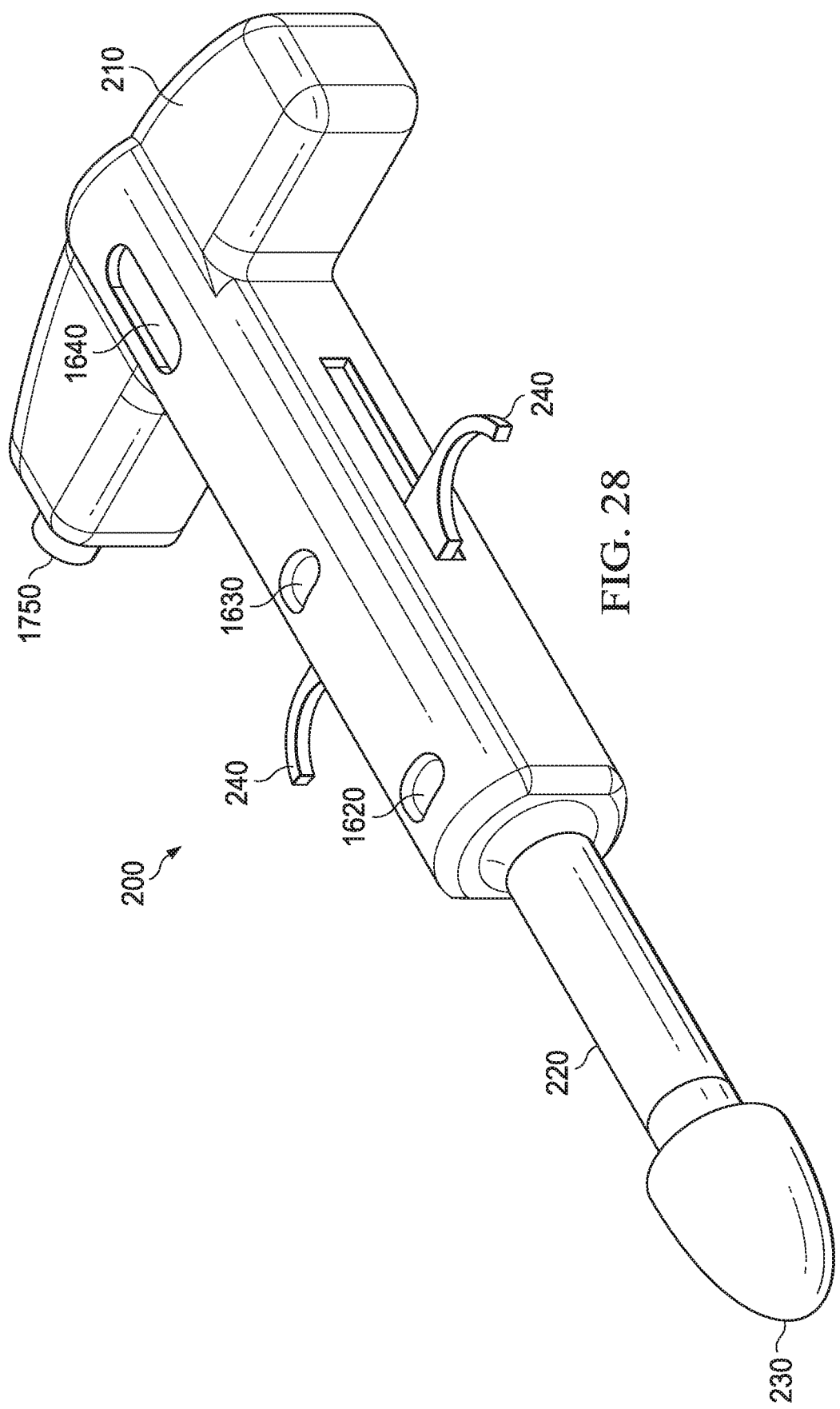
Figure 29:
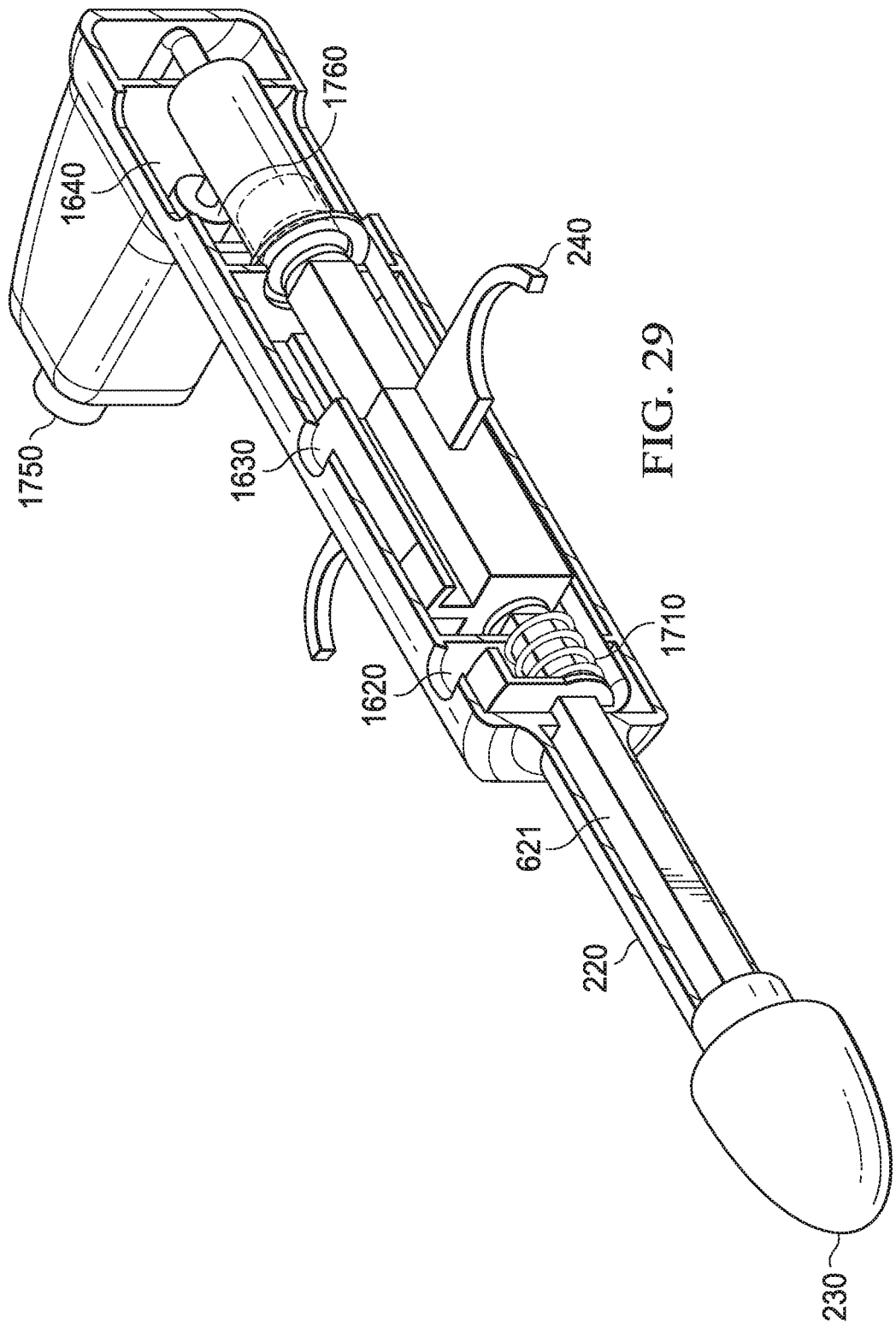
Figure 30A:
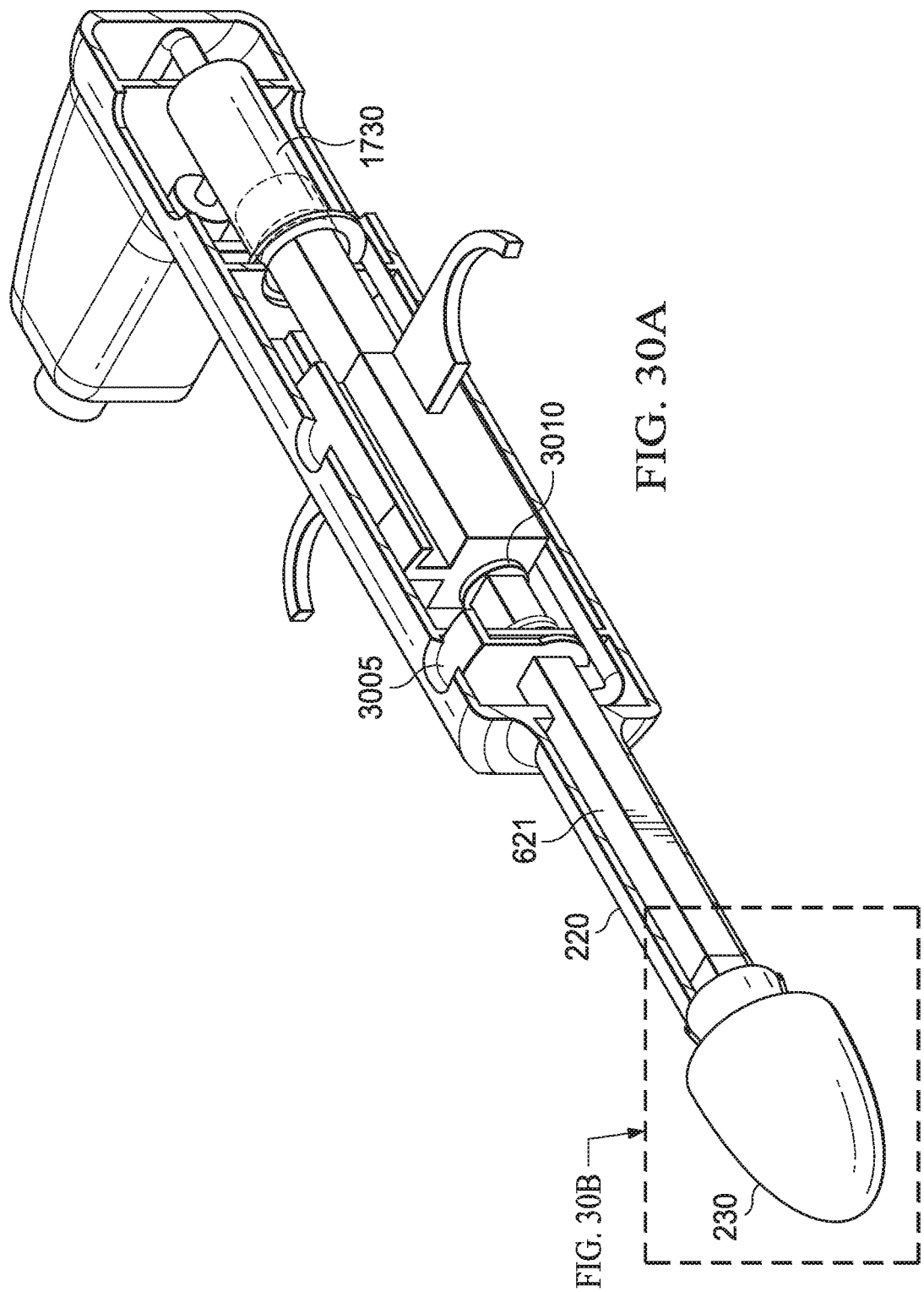
Figure 30B:
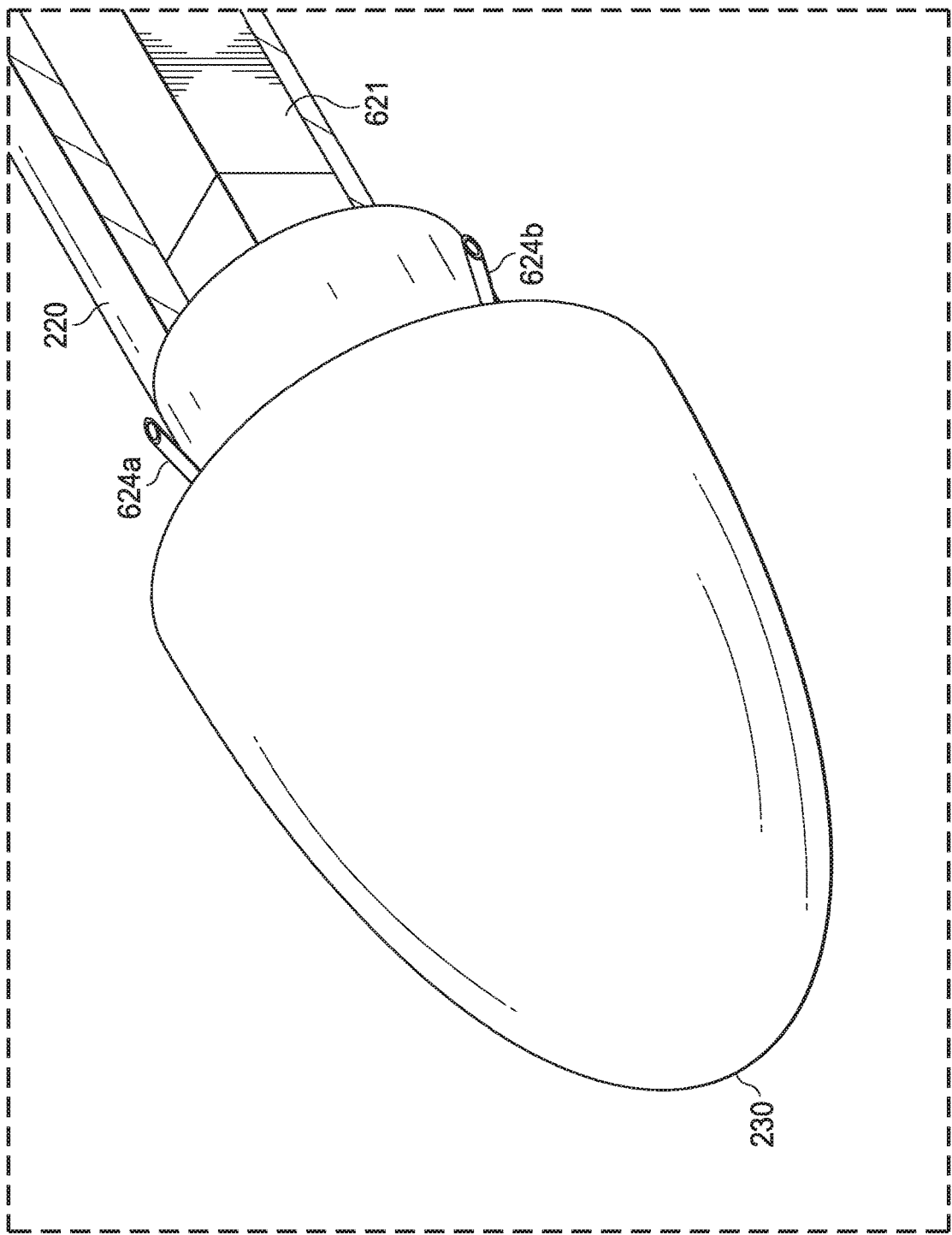
Figure 31:
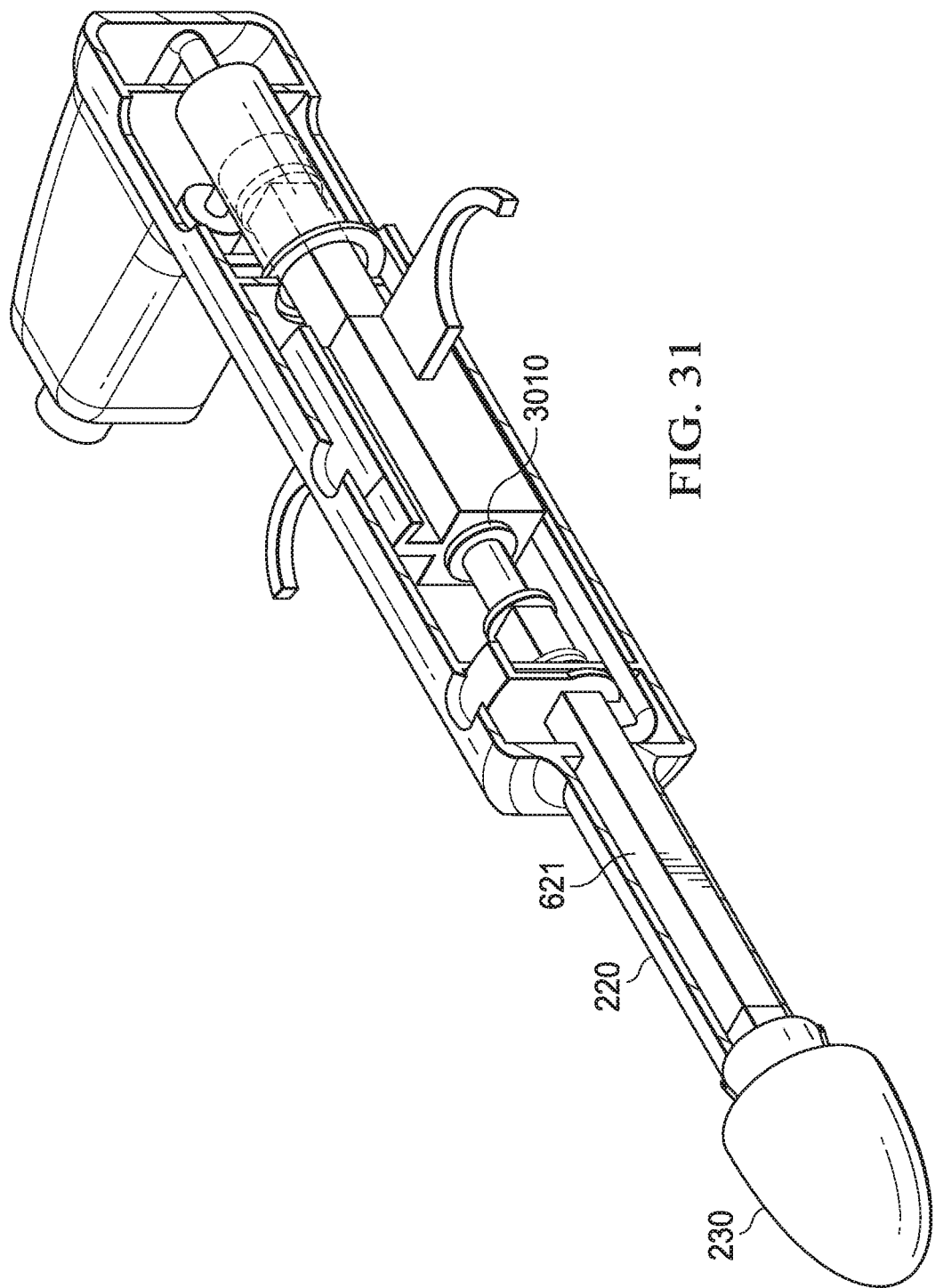
Figure 32:
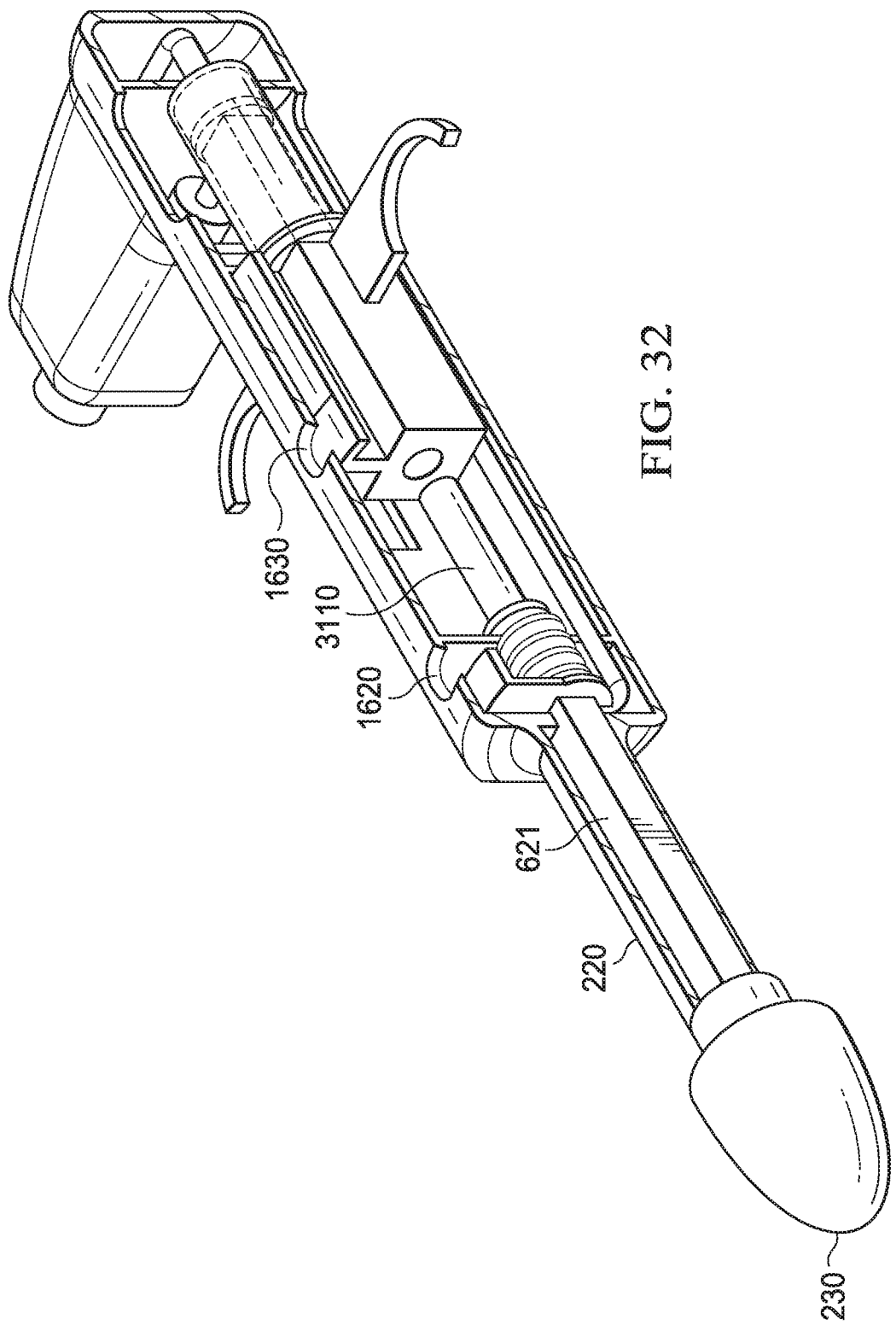
Figure 33C:
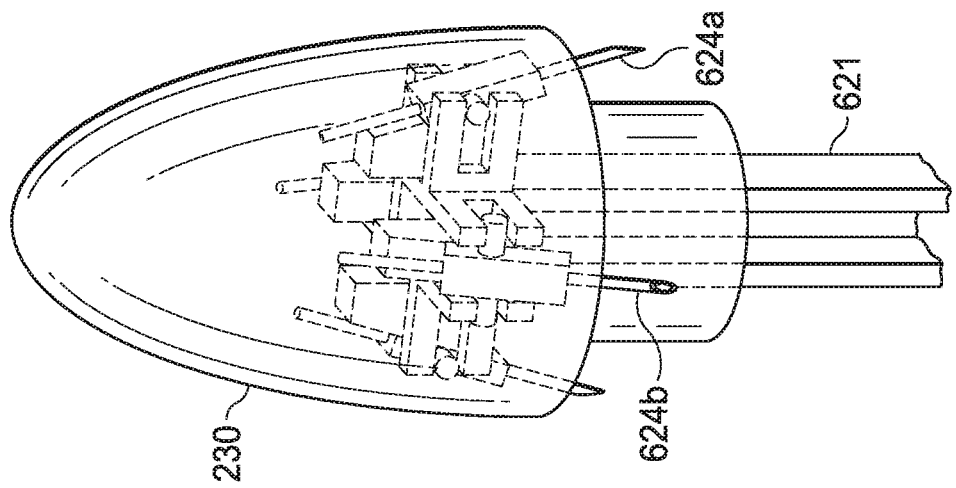
Figure 33B:
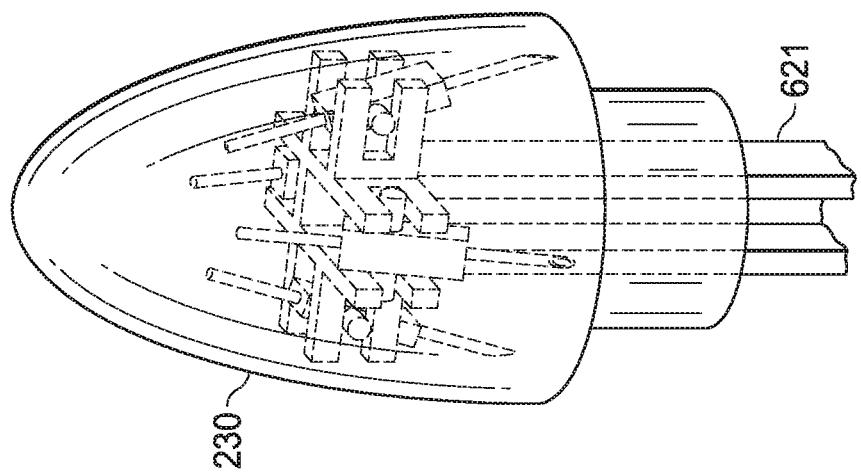
Figure 33A:
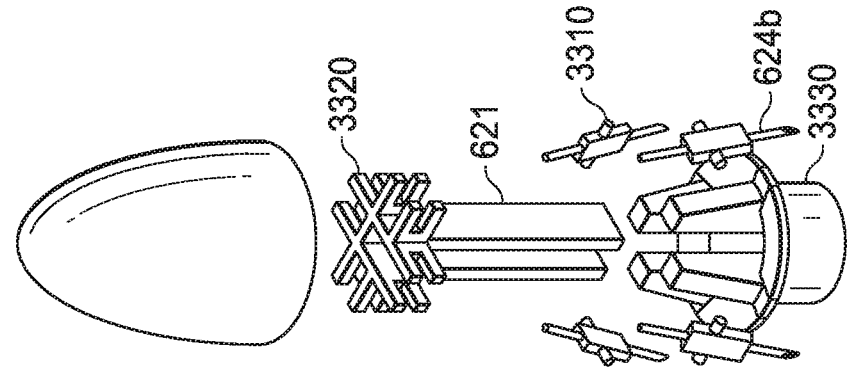
Figure 34:
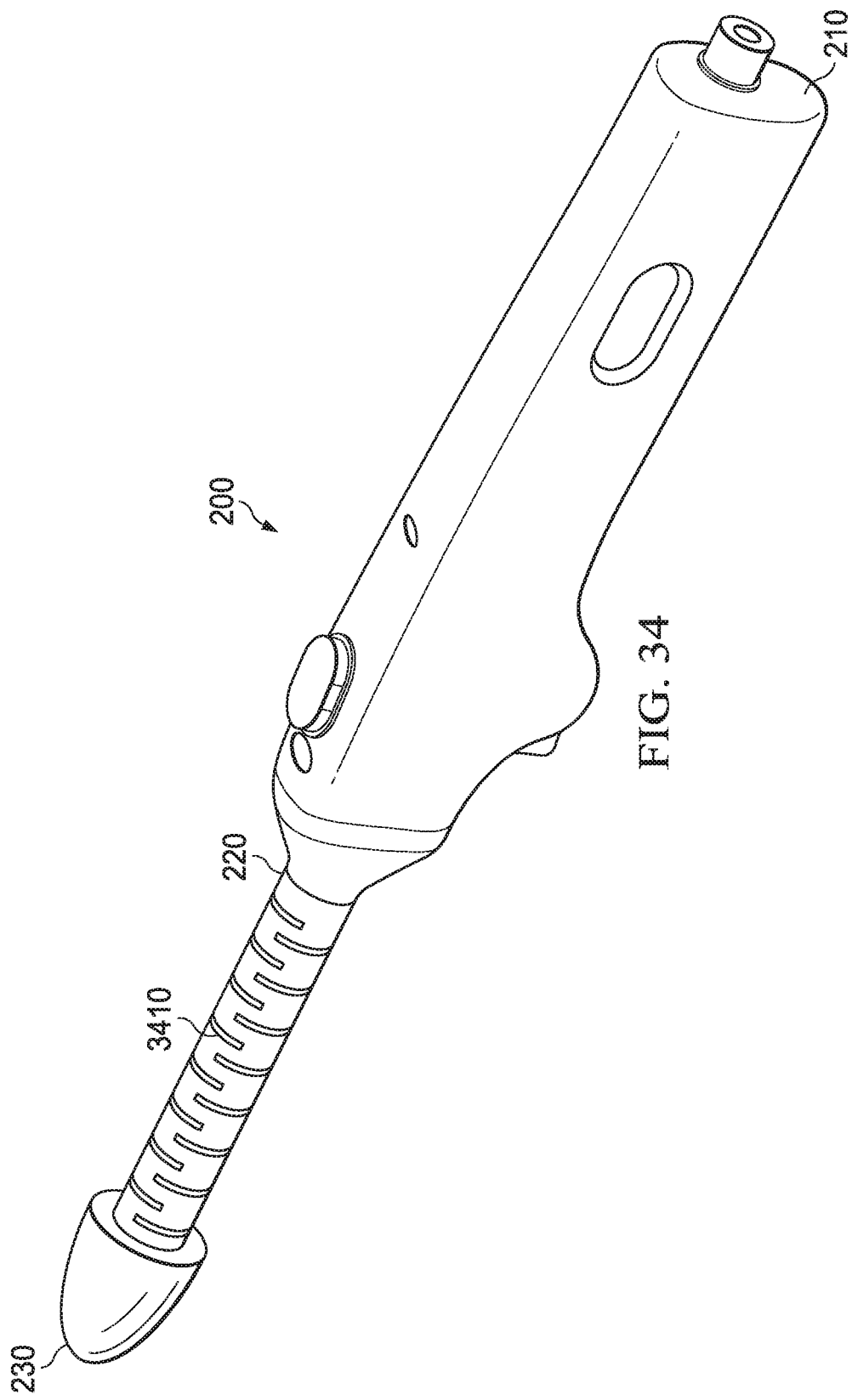
Figure 35:
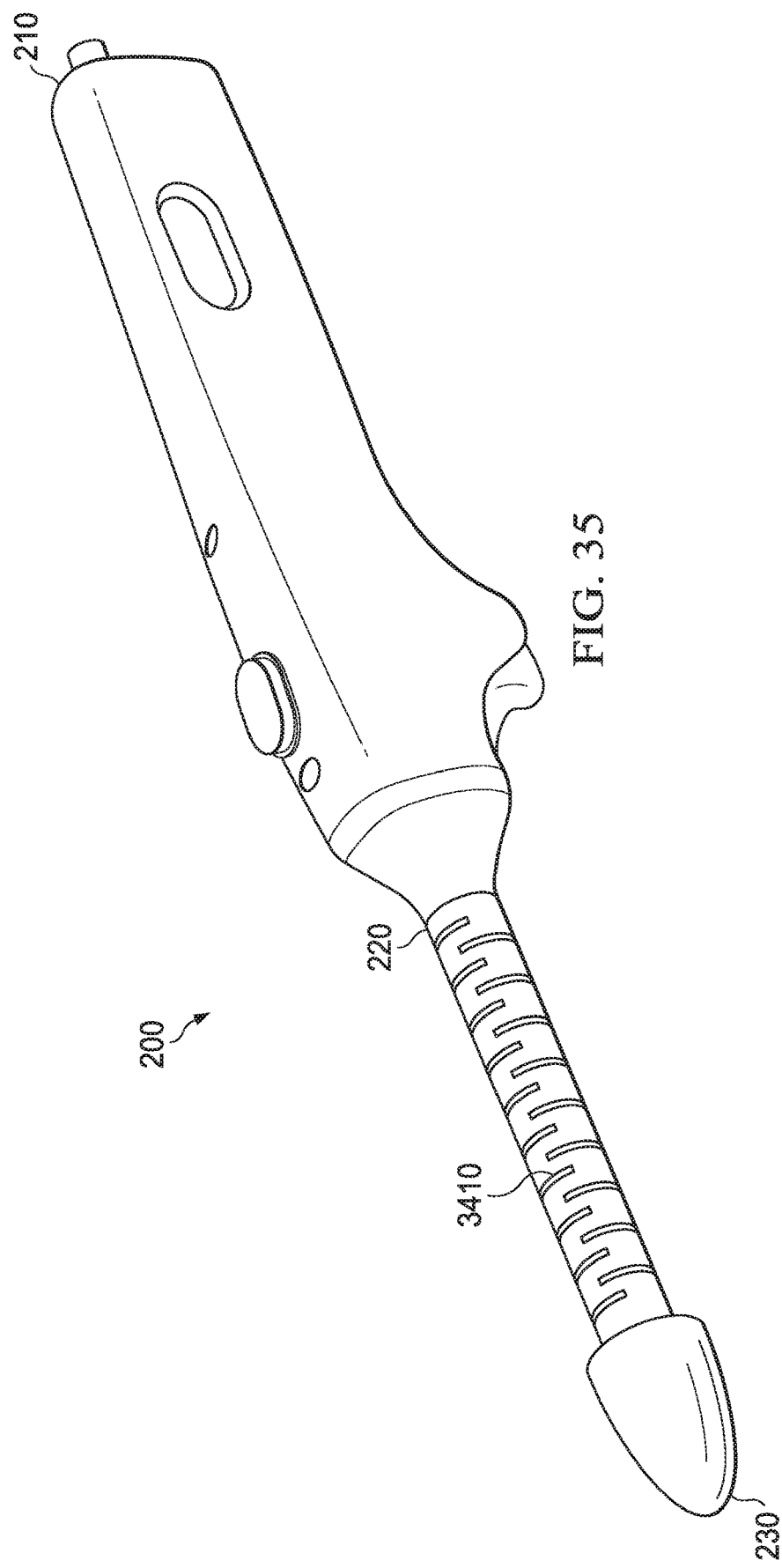
Figure 36:
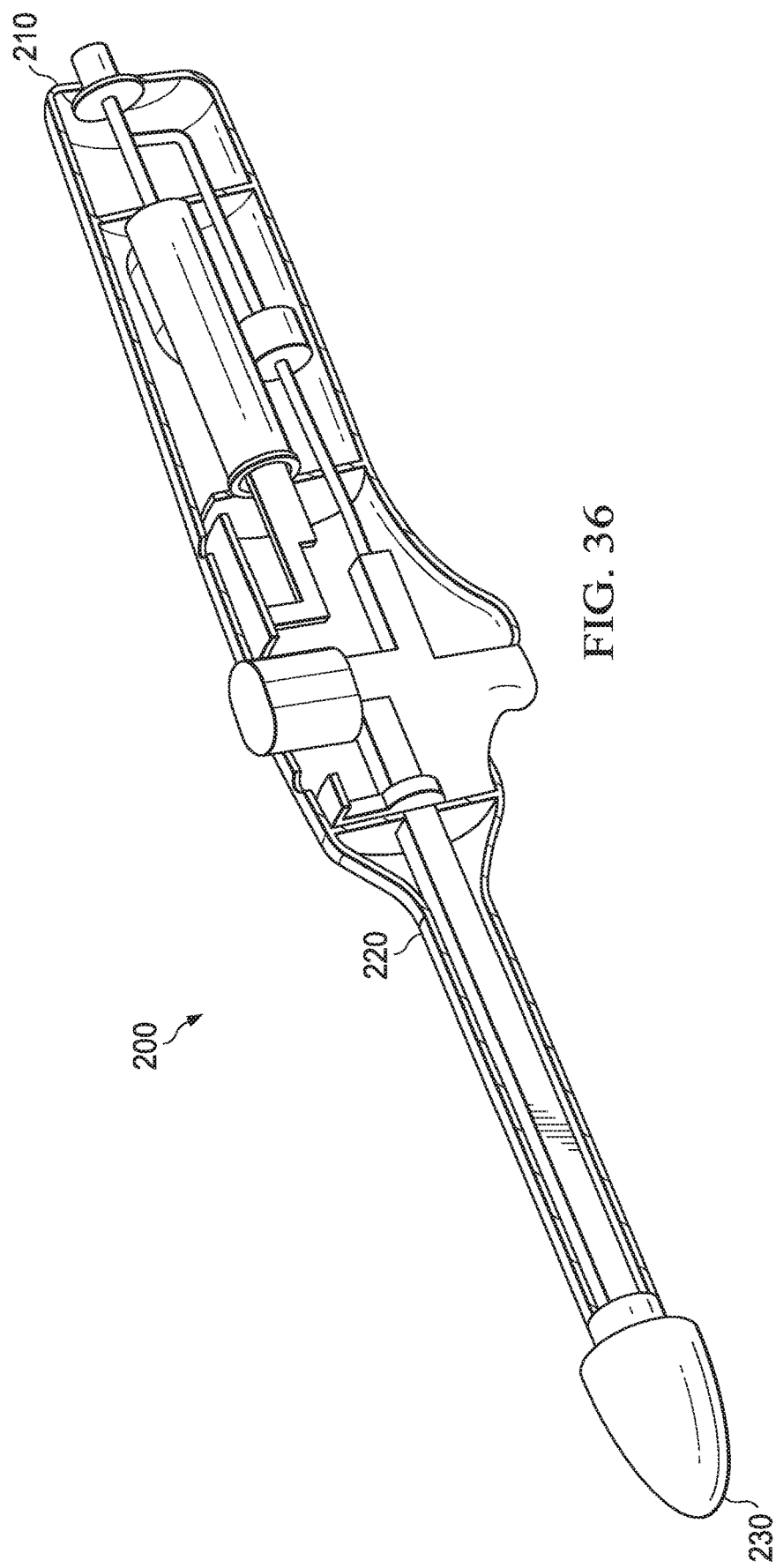
Figure 37A:
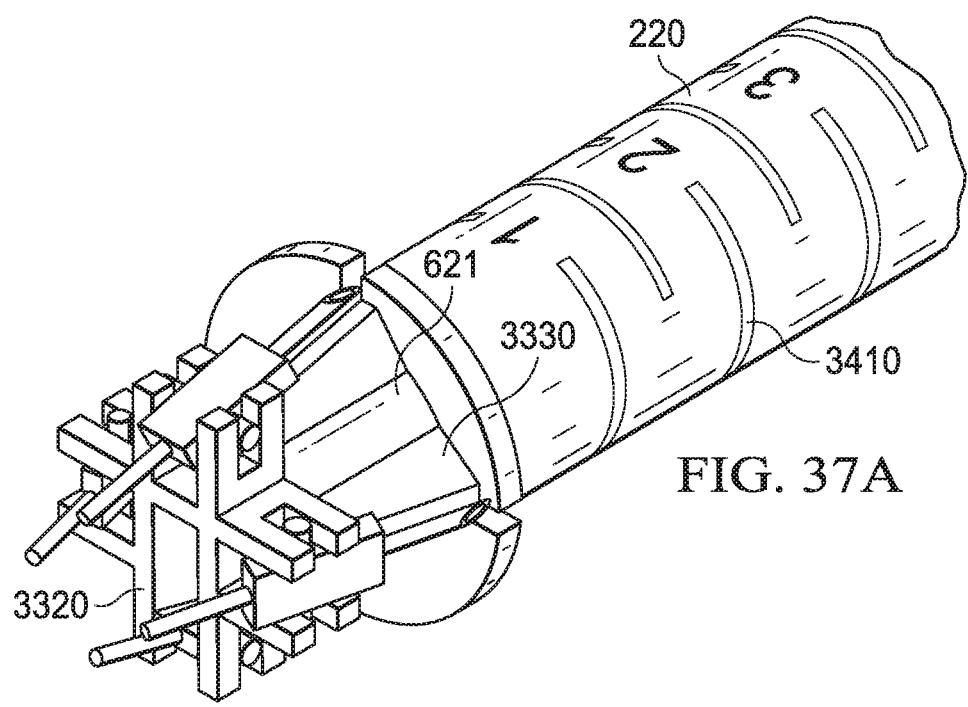
Figure 38:
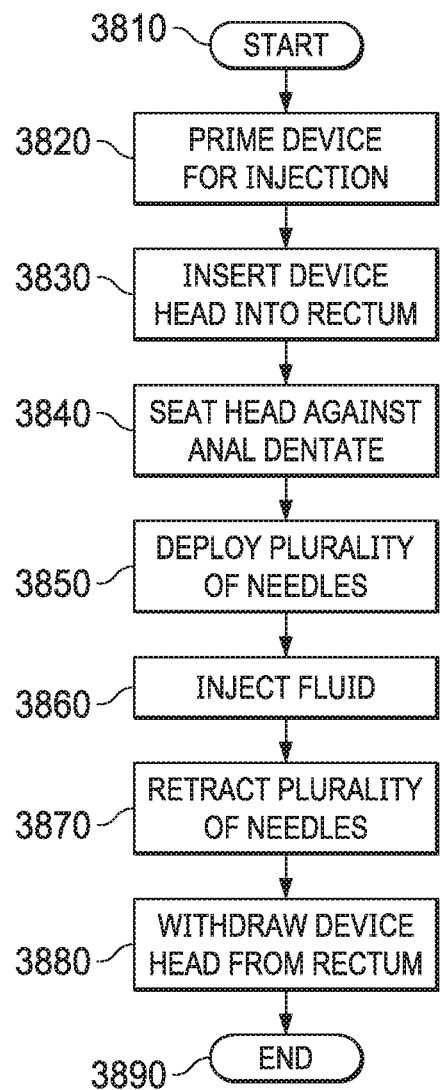

FIGS. 18A-C are isometric views of a Luer activated fill port;

FIGS. 19A and B are schematic views of two alternative priming systems;

FIGS. 20A and B are respective isometric cutaway views of the linear embodiment of FIG. 16 and a head thereof;

FIGS. 21A and B are respective isometric cutaway views of the linear embodiment of FIG. 16 and a handle thereof;

FIGS. 22A and B are respective isometric cutaway views of the linear embodiment of FIG. 16 and a handle thereof;

FIG. 23 is an isometric view of a pistol-handle embodiment of a rectal injection device;

FIG. 24 is an isometric cutaway view of the pistol-handle embodiment of FIG. 23;

FIGS. 25A-C are respective isometric cutaway views of the pistol-handle embodiment of FIG. 23 and a head and handle thereof;

FIG. 26 is an isometric cutaway view of the pistol-handle embodiment of FIG. 23;

FIGS. 27A and B is an isometric cutaway view of the pistol-handle embodiment of FIG. 23 and a handle thereof;

FIG. 28 is an isometric view of a T-handle embodiment of a rectal injection device;

FIG. 29 is an isometric cutaway view of the T-handle embodiment of FIG. 28;

FIGS. 30A and B are respective isometric cutaway views of the T-handle embodiment of FIG. 28 and a head thereof;

FIG. 31 is an isometric cutaway view of the T-handle embodiment of FIG. 23;

FIG. 32 is an isometric cutaway view of the T-handle embodiment of FIG. 23;

FIGS. 33A-C are respective views of one embodiment of a rectal injection device head;

FIG. 34 is an isometric view of a linear embodiment of a rectal injection device;

FIG. 35 is an isometric view of the linear embodiment of FIG. 34 from another angle;

FIG. 36 is an isometric cutaway view of the linear embodiment of FIG. 34;

FIGS. 37A and B are cutaway views of a head of the rectal injection device of FIG. 34; and FIG. 38 is a flow diagram of one embodiment of a method of using a rectal injection device.

DETAILED DESCRIPTION

Introduced herein are various embodiments of a device and method for injection to address hemorrhoids, fecal incontinence caused by anal sphincter relaxation or other concerns. Many of the various embodiments are used as follows: (1) a head of the device is inserted into the rectum of a subject animal or human past the anal dentate line; (2) the device is then pulled back until the head contacts the dentate and internal anal sphincter; (3) multiple needles are deployed into the rectum around the internal sphincter using an actuator of some type; (4) a liquid, which may be a filler agent, a sclerosing agent, or a liquid of another type that depends upon the desired treatment, is injected through the needles into or around the internal sphincter port; (5) the needles are retracted; and (6) the device is withdrawn. In certain embodiments, the head is or becomes enlarged in terms of its diameter such that it seats against the internal sphincter. This allows a clinician operating the device some assurance that the head is properly located within the patient without needing to see the head, e.g., using a scope). Of course, a scope may be employed.

In certain embodiments, the head is bulbous. In other embodiments, the head is conical or frustoconical.

In certain other embodiments, the device employs the multiple needles to inject multiple evenly spaced regions of the rectum with a single pass. In certain embodiments, the needles translate to deploy and retract. In other embodiments, the needles rotate to deploy and retract. In certain embodiments, a radial flange drives the needles. In other embodiments, a cam drives the needles. In yet other embodiments, one or more sliding linkages drive the needles. In some embodiments, the needles are spring-loaded. In a few embodiments, the needles are spring-loaded such that they retract in the absence of another force.

In certain embodiments, the needles are evenly radially spaced; e.g., four needles being spaced 90° apart to form four quadrants for injection of liquid. In alternative embodiments, the needles are unevenly spaced. These embodiments may be useful in the treatment of conditions not benefitting from, or not requiring, uniform injection. In related embodiments, four needles are provided. In other embodiments, different numbers of needles are provided.

In many embodiments, a central member drives the sliding block, cam or sliding linkage(s), allowing the needles to deploy and retract concurrently. In many embodiments, a trigger or other manual actuator is coupled to the central member, allowing the clinician to deploy and retract the needles.

In many embodiments, at least one reservoir contains the liquid that is ultimately injected through the needles. Passages couple the reservoir(s) to the needles, allowing the liquid to flow from the reservoir(s) to the needles. In certain embodiments, the reservoir(s) are formed of one or more syringes, which may be conventional or custom-made for the device. The passages may be common to multiple needles, e.g., one passage for two needles or one passage for eight needles, or may correspond one-for-one with the needles, e.g., four passages for four needles.

In one embodiment, the device may be used to provide an improved drug delivery method in the treatment of gastrointestinal muscle disorders and other smooth muscle dysfunction by the injection of a therapeutically effective amount of sphincteric botulinum toxin or related compounds, with an improvement in efficacy provided by the plurality of needles and plurality of injection sites provided by the device. The improved efficacy provided by plurality of needles embodied in the device, versus a single needle, may be thus used in the improved treatment of various disease conditions, including achalasia, disorders of the lower esophageal sphincter, gastroparesis, hypertrophic pyloric stenosis, sphincter of Oddi dysfunction, short-segment Hirschsprung's, anal fissure, hemorrhoids, proctalgia fugax, irritable bowel syndrome, disorders of the upper esophageal sphincter, vasospastic disorders, and disorders of uterine and bladder spasm.

In another embodiment, the device may be used for the purpose of providing for SCL for esophageal varices.

In another embodiment, an optical endoscopic functionality may be integrated with the injection array device to aid in the accurate location of injection sites, and to provide visualization of the injection site during injection and drug administration. A sufficiently low-cost camera may be used in this integration to enable the cost-effective one-time-use of the device.

In another embodiment, the device may be used in providing an improved method of drug delivery used in the treatment of for treatment of esophageal cancer. In this embodiment, the device provides an improved means for the injection of certain light-sensitive materials used for photodynamic therapy, or for the delivery of chemotherapy or other medications to the tumor location.

Figure 1:
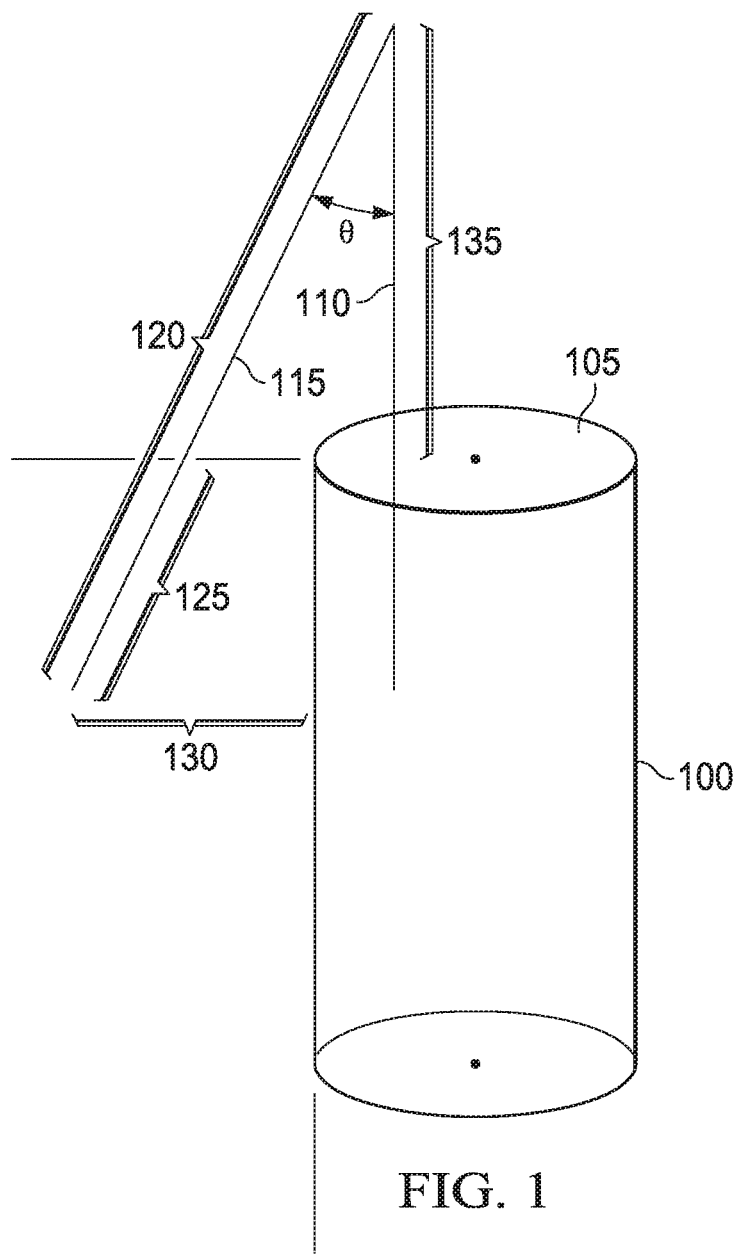
FIG. 1 is a diagram of geometry involved in some embodiments of a rectal injection device.

FIG. 1 is a diagram of geometry involved in some embodiments of a rectal injection device. A cylinder 100 having, for example, a 10 mm radius, represents an anal canal of a subject patient. An upper end 105 of the cylinder 100 represents an anal dentate of the anal canal 100. A line 110 represents an extension tube (not shown) of an injection device (not shown) passing through the anal canal 100 along an axis parallel thereto and exiting the anal dentate into the rectum (not shown). A line 115 represents a needle extending from a head (not shown) of the rectal injection device. The line has a length 120 and a penetration depth 125. The line 115 is at a departure angle θ from the line 110. In various embodiments for treatment of hemorrhoids or fecal incontinence, θ typically ranges from about 0° to about 90°. However, in other embodiments, θ exceeds 90°. FIG. 1 is directed to rotating-needle embodiments (in which θ changes between deployed and retracted positions). Accordingly, FIG. 1 indicates an x-distance 130 by which a tip of the needle moves as it is rotated between a retracted and a deployed position. A root of the needle (the end opposite the tip) is displaced from the anal dentate by a y-distance 135.

In one embodiment, the rectal injection device has an extension tube length of greater than 5 cm and a diameter of less than or equal to 3 cm. In this embodiment, the head houses three to five needles of 23-25 gauge that may be controlled individually or in tandem. The head is designed to seat at or near the dentate line without a camera, and have a rounded (bulbous, conical or frustoconical) head shape. It employs a downward injection angle from above the dentate line, has an injection depth 125 of 4-5 mm, and have a needle departure angle θ of less than 45°.

Figure 2:
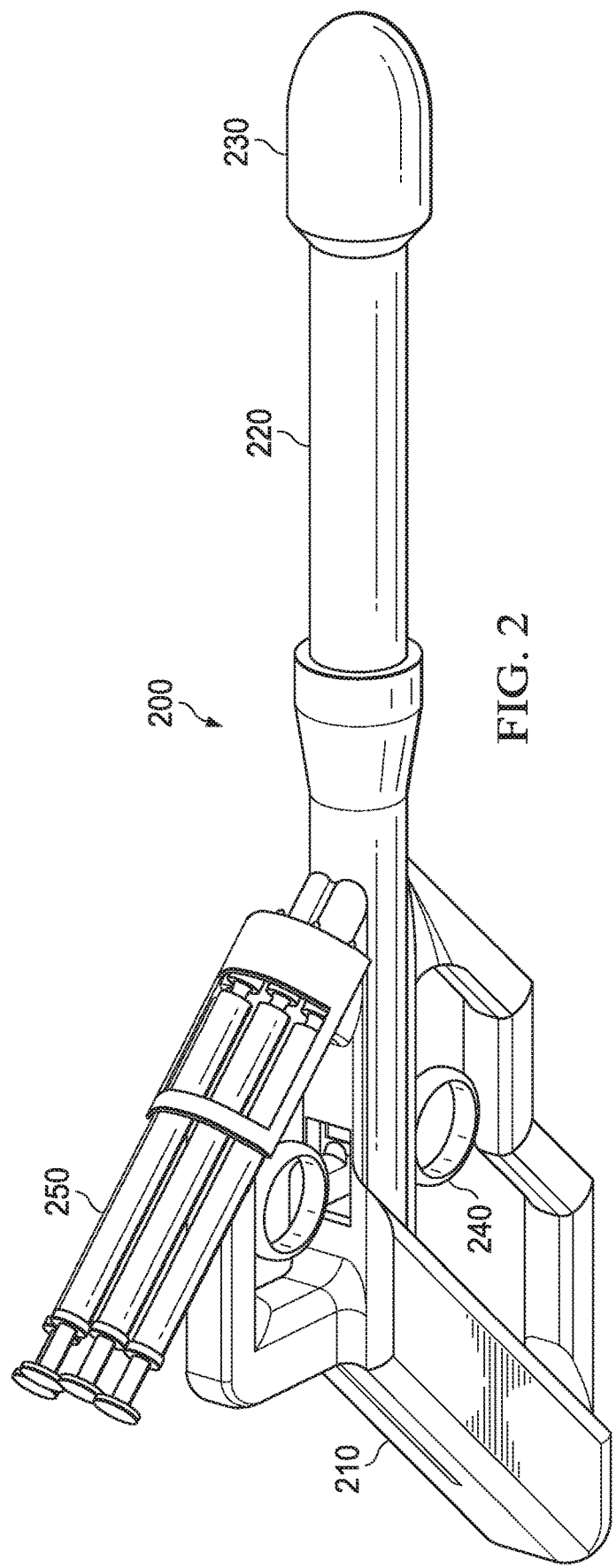
FIG. 2 is a diagram showing one embodiment of a rectal injection device.

FIG. 2 is a diagram showing one embodiment of a rectal injection device 200. In this embodiment, the device 200 resembles a pistol. Accordingly, the device has a handle 210. The handle 210 is configured to be gripped by a human hand, allowing a clinician to control the device 200. The device 200 further has an extension tube 220 that extends forward from the handle 210 and terminates in a head 230 at an end of the extension tube 220 that is distal from the handle 210. The device 200 further has a trigger 240 (including two distinct finger loops shown but not separately referenced in this embodiment) that may be translated back toward the handle 210 or forward toward the head 230 to deploy and retract needles (not shown) that are associated with the head 230 and at least one reservoir 250 for containing a liquid (not shown) and eventually dispensing it through the needles into a patient (not shown). The embodiment of FIG. 2 shows four reservoirs 250 having plungers and therefore taking the form of syringes. In the embodiment of FIG. 2, each plunger is independently translatable; a clinician can cause each syringe to dispense separately. In an alternative embodiment, the plungers are ganged, e.g., with a common pusher (not shown), to allow a clinician to cause the syringes to dispense concurrently by actuating the common pusher. "Trigger" is broadly defined to include any structure configured for external actuation, whether it be by human (e.g., finger or hand) or machine (e.g., air hose or motor).

Figure 3:
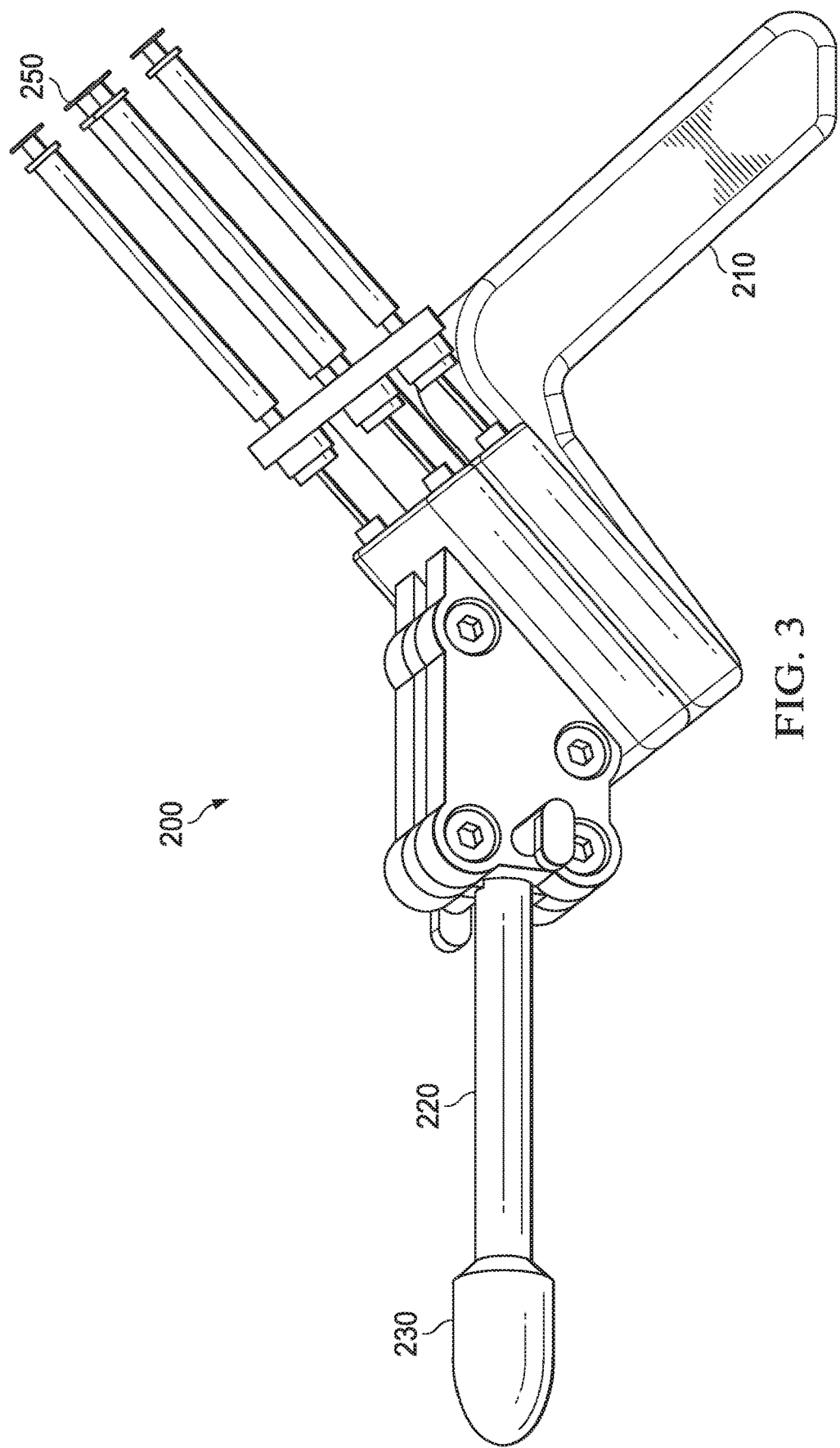
FIG. 3 is a diagram showing another embodiment of a rectal injection device.

FIG. 3 is a diagram showing another embodiment of a rectal injection device 200. Again, the device 200 is pistol-like, but less so than the embodiment of FIG. 2. As before, the device 200 has a handle 210 allowing a clinician to control the device 200, an extension tube 220 that extends forward from the handle 210 and supports a head 230 at an end of the extension tube that is distal from the handle 210, and at least one reservoir 250 for containing a liquid and eventually dispensing it through needles (not shown) into a patient (not shown). As with the embodiment of FIG. 2, the embodiment of FIG. 3 shows four reservoirs 250 having plungers and therefore taking the form of syringes. As with the embodiment of FIG. 2, each plunger is independently translatable; a clinician can cause each syringe to dispense separately. In an alternative embodiment, the plungers are ganged, e.g., with a common pusher (not shown), to allow a clinician to cause the syringes to dispense concurrently by actuating the common pusher. The embodiment of FIG. 3 does not show a trigger. However, the embodiment of FIG. 3 would include a mechanism for deploying and retracting the needles in the head 230.

Several embodiments of the head 230 of FIGS. 2 and 3 will now be illustrated and described. In general, the head 230 is intended to enter the rectum through the anus, be lodged against the anal dentate and contain needles that are to be deployed to effect injection and treatment and retracted to allow the head 230 to be withdrawn from the rectum.

Figure 4:
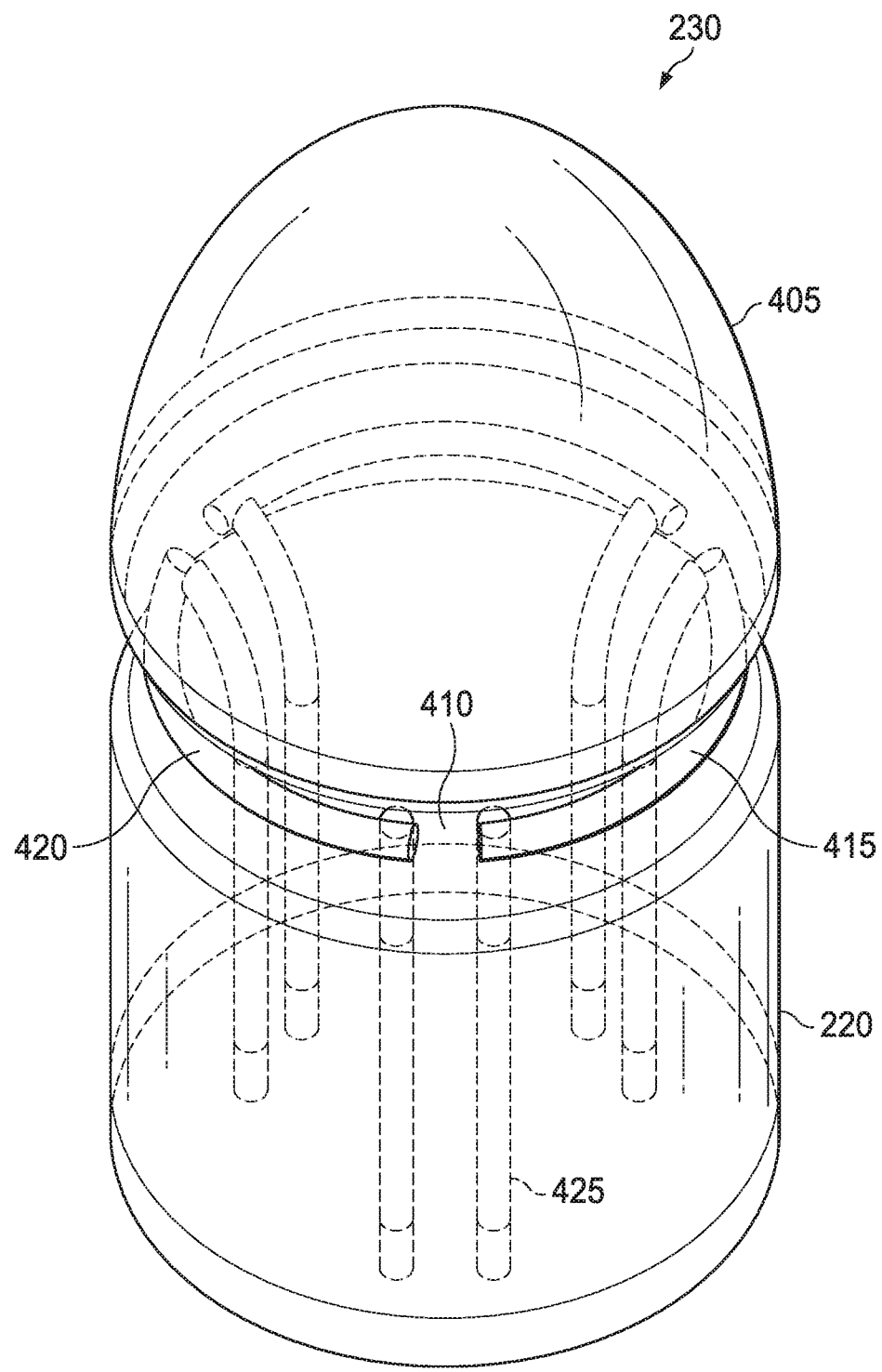
FIG. 4 is an isometric view of a balloon embodiment of a head of a rectal injection device in a deflated state.
Figure 5:
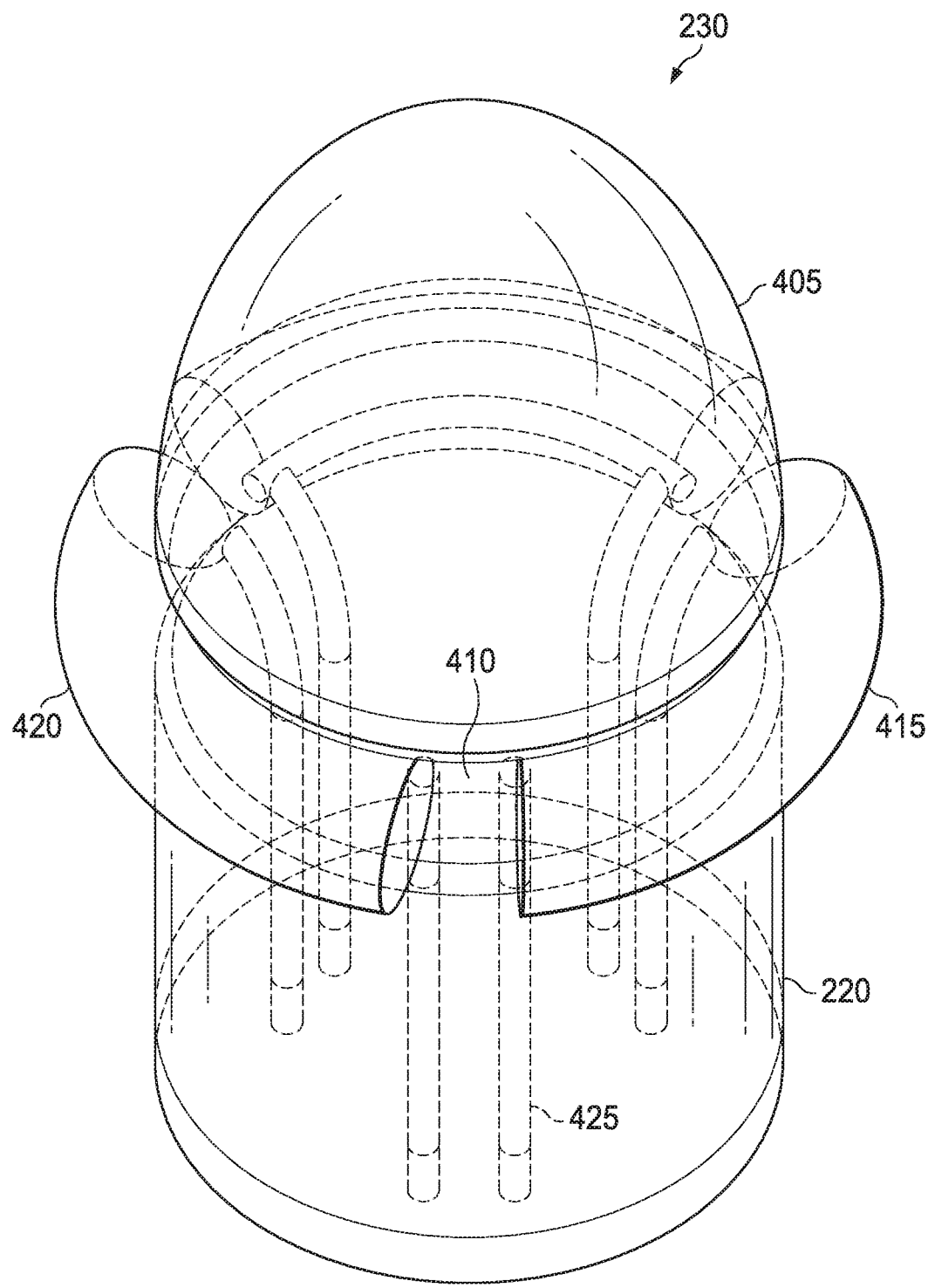
FIG. 5 is an isometric view of the balloon embodiment of FIG. 4 in an inflated state.

FIG. 4 is an isometric view of a balloon embodiment of a head 230 of a rectal injection device (e.g., 200 of FIGS. 2 and 3) in a deflated state. In the embodiment of FIG. 4, the head 230 has a generally spherical end 405 and an annular recess 410 under the generally spherical end 405 according to the view of FIG. 2. Balloon segments (two of which being referenced 415, 420) reside in the annular recess 410. Passages (shown in broken line, and one of which being referenced 425) allow a gas (e.g., air) to be introduced into, and withdrawn from, the balloon segments 415, 420, causing them to inflate and deflate. FIG. 5 is an isometric view of the balloon embodiment of FIG. 4 in an inflated state.

FIGS. 4 and 5 also show a portion of the extension tube 220 under the annular recess 410 according to the view of FIGS. 4 and 5. It will be noted that the generally spherical end 405 is about as wide as the extension tube 220 (i.e. the radius of the generally spherical end 405 is approximately the same as the radius of the extension tube 220). Because the generally spherical end 405 is not substantially wider than the extension tube 220, rectal insertion is expected to be easier and more comfortable to the patient. However, the balloon segments 415, 420 (or some kind of radial extension) are needed to ensure that the generally spherical end 405 is not inadvertently withdrawn before treatment is complete. Embodiments of the head 230 to be illustrated and described below are wider than the extension tube 220 such that its width requires a force to withdraw the head 230 from the rectum. This, in turn, eliminates a need for the balloon segments 415, 420.

Figure 6:
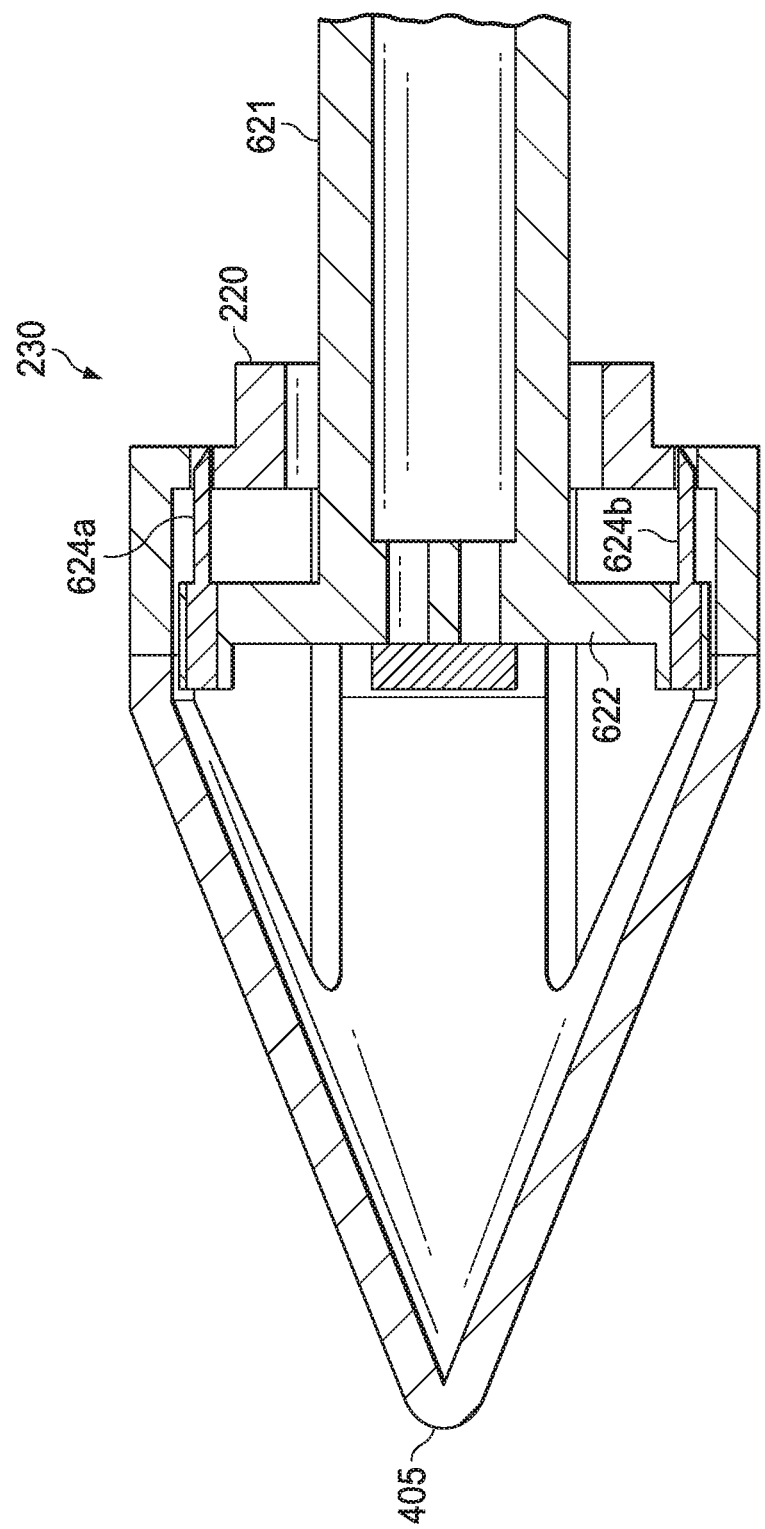
FIG. 6 is a sectional view of one translating-needle embodiment of a head of a rectal injection device in a retracted position.
Figure 7:
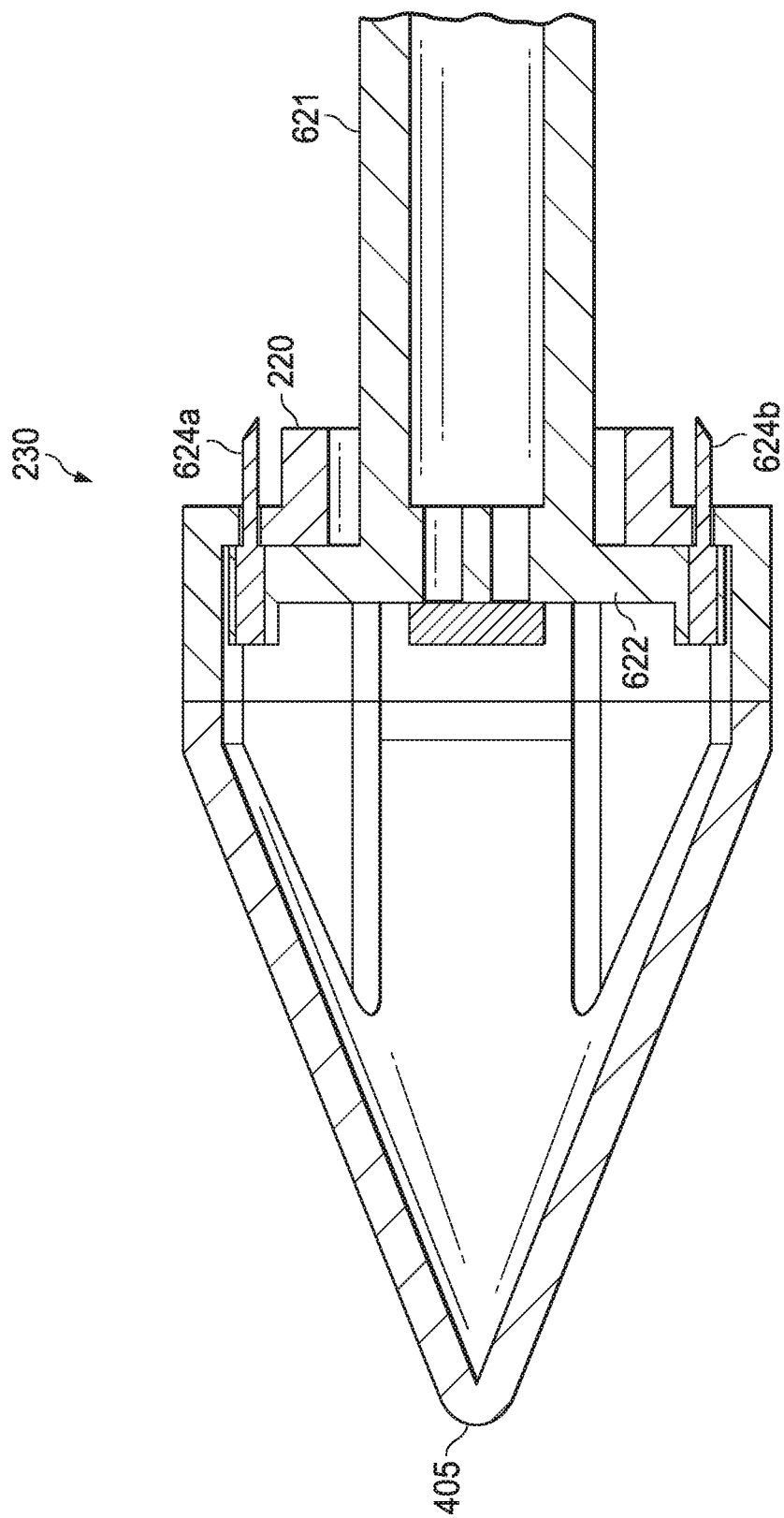
FIG. 7 is a sectional view of the translating-needle embodiment of FIG. 6 in a deployed position.

FIG. 6 is a sectional view of one translating-needle embodiment of a head 230 of a rectal injection device (e.g., 200 of FIGS. 2 and 3) in a retracted position. It should be noted that the head 230 is generally conical or frustoconical and wider than the extension tube 220. A pullrod 621 is located in the extension tube 220. The pullrod 621 terminates in a radial flange 622 that bears against spring-loaded needles 624a, 624b so that, when the pullrod 621 is pulled (moved to the right in the view of FIG. 6), the radial flange 622 moves to the right and urges the needles 624a, 624b from their retracted position as shown in FIG. 6 to a deployed position. FIG. 7 is a sectional view of the translating-needle embodiment of FIG. 6 showing the needles 624a, 624b in their deployed position. Note that the angle θ of the needles 624a, 624b relative to the axis of the extension tube 220 is about 0°. "Pullrod" is defined broadly herein to include any structure that couples needles to a trigger, whether or not the pullrod pulls, pushes, rotates or moves laterally to deploy the needles.

Figure 8:
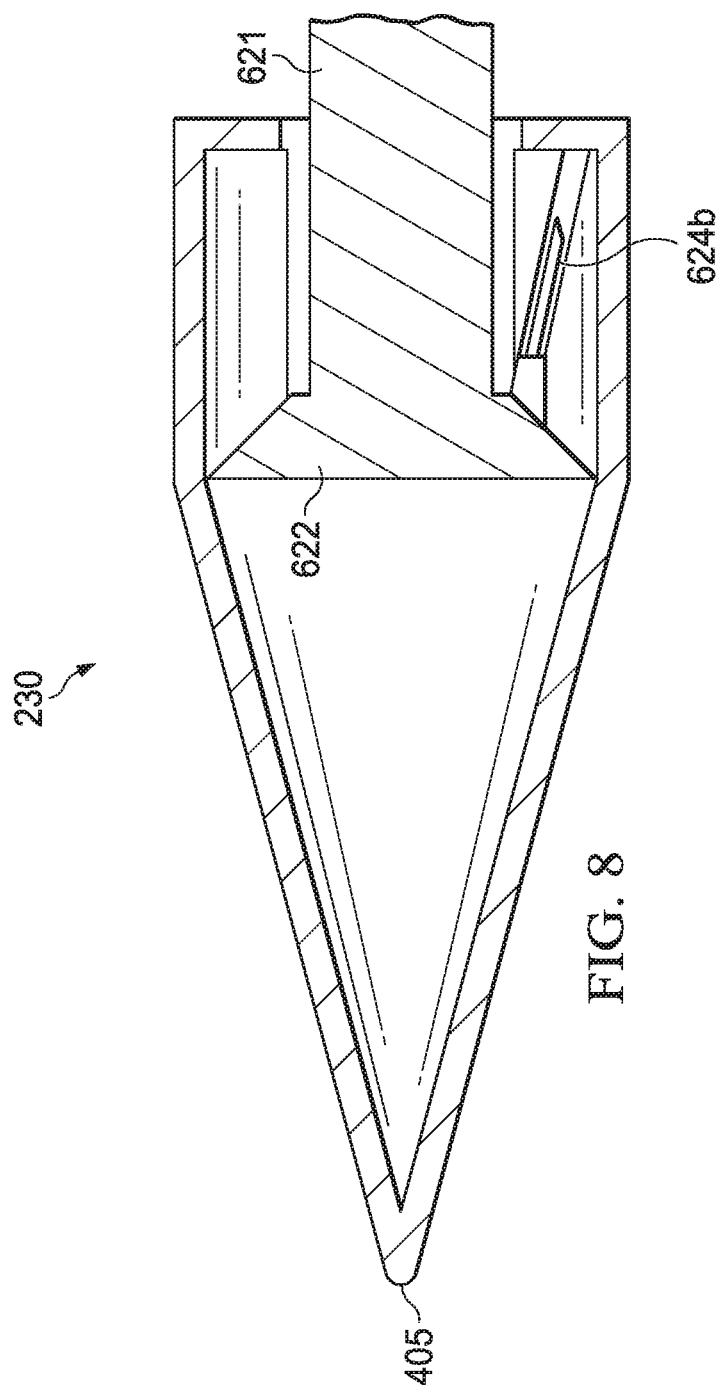
FIG. 8 is a sectional view of another translating-needle embodiment of a head of a rectal injection device in a retracted position.
Figure 9:
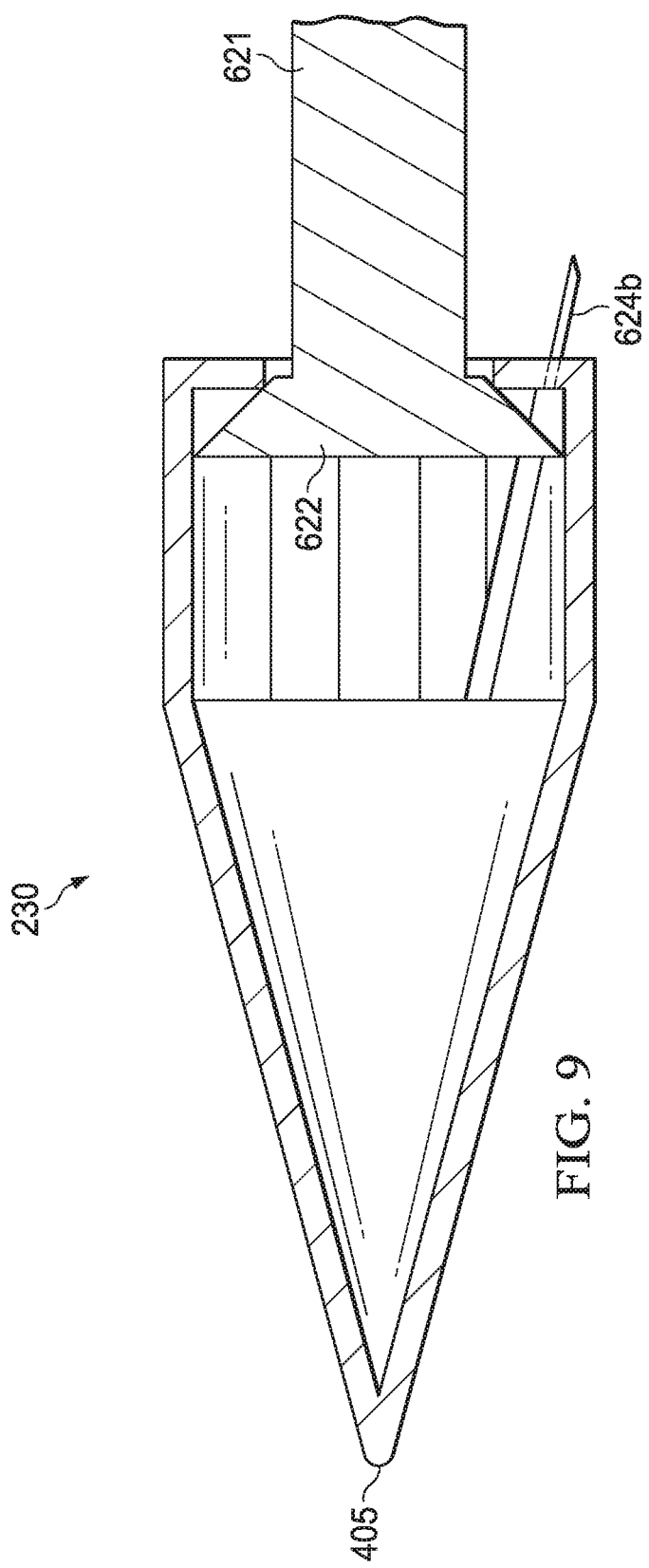
FIG. 9 is a sectional view of the translating-needle embodiment of FIG. 8 in a deployed position.

FIG. 8 is a sectional view of another translating-needle embodiment of a head 230 of a rectal injection device (e.g., 200 of FIGS. 2 and 3) in a retracted position. Again it should be noted that the head 230 is generally conical or frustoconical. Though FIG. 8 does not show the extension tube, the head 230 is wider than the extension tube. A pullrod 621 is located in the extension tube 220. The pullrod 621 terminates in a radial flange 622 having a conical backside (not separately referenced) that bears against spring-loaded needles (only one of which being shown and referenced as 624b) so that, when the pullrod 621 is pulled (moved to the right in the view of FIG. 8), the radial flange 622 moves to the right and urges the needles (e.g., 624b) from their retracted position as shown in FIG. 8 to a deployed position. FIG. 9 is a sectional view of the translating-needle embodiment of FIG. 8 showing the needles (e.g., 624b) in their deployed position. Note that the angle θ of the needles (e.g., 624b) relative to the axis of the extension tube 220 is between about 10° and about 30°.

Figure 10:
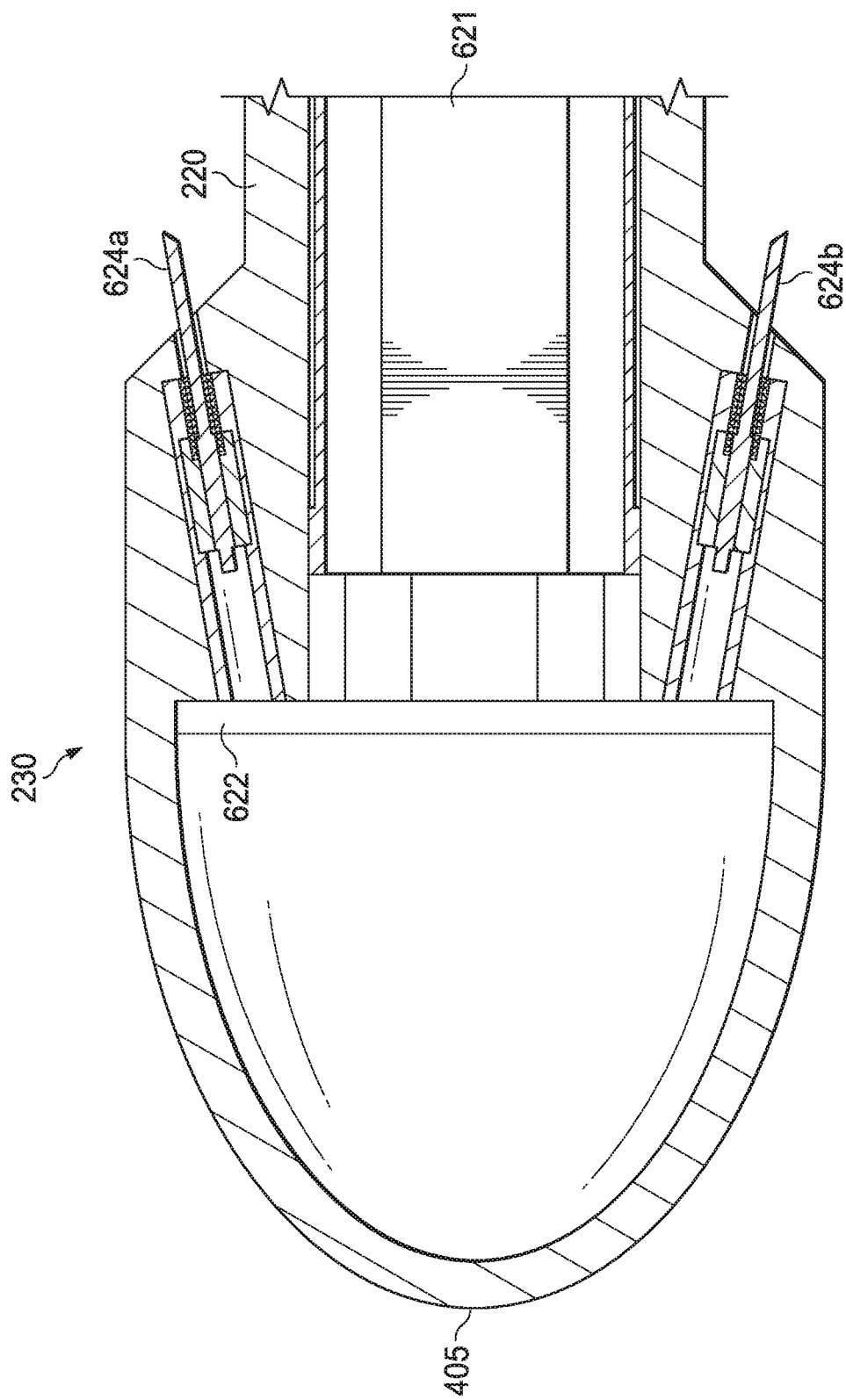
FIG. 10 is a sectional view of yet another translating-needle embodiment of a head of a rectal injection device in a deployed position.

FIG. 10 is a sectional view of yet another translating-needle embodiment of a head 230 of a rectal injection device (e.g., 200 of FIGS. 2 and 3) in a deployed position. Unlike the embodiments of FIGS. 6 and 8, the embodiment of FIG. 10 has a generally spherical end 405. Unlike the embodiment of FIGS. 4 and 5, the spherical end 405 is substantially wider than the extension tube 220; thus balloon segments (or some other structure to hold the head 230 in place relative to the rectum) are not needed. The pullrod 621 terminates in a radial flange 622 having a backside (not separately referenced) that bears against spring-loaded needles 624a, 624b so that, when the pullrod 621 is pulled (moved to the right), the radial flange 622 moves to the right and urges the needles 624a, 624b from their retracted position (not shown) to a deployed position (shown). Note that, as with the embodiment of FIG. 8, the angle θ of the needles 624a, 624b relative to the axis of the extension tube 220 is between about 10° and about 30°.

Figure 11:
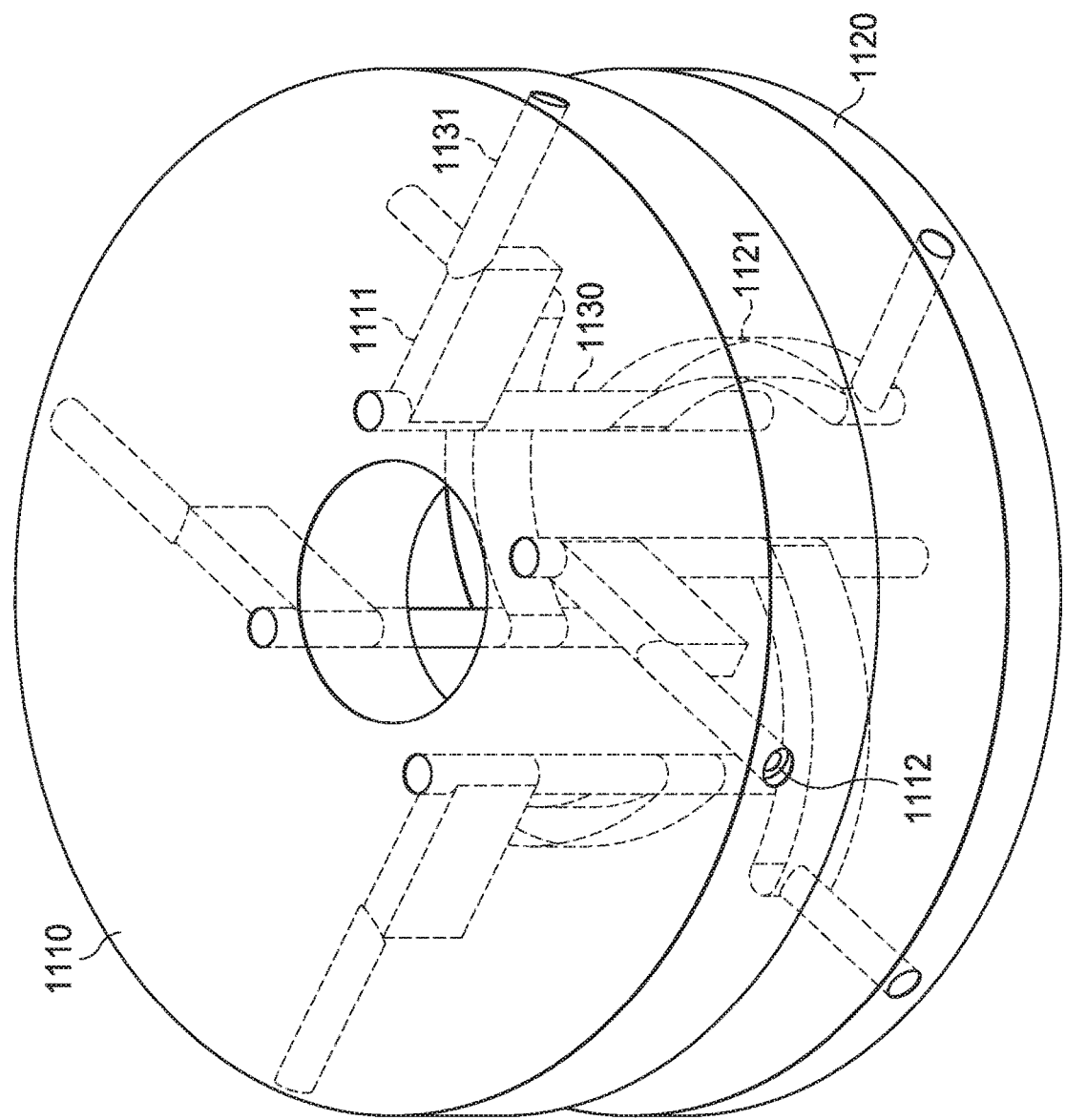
FIG. 11 is an isometric view of a cam-driven embodiment of a head of a rectal injection device in a retracted position.
Figure 12:
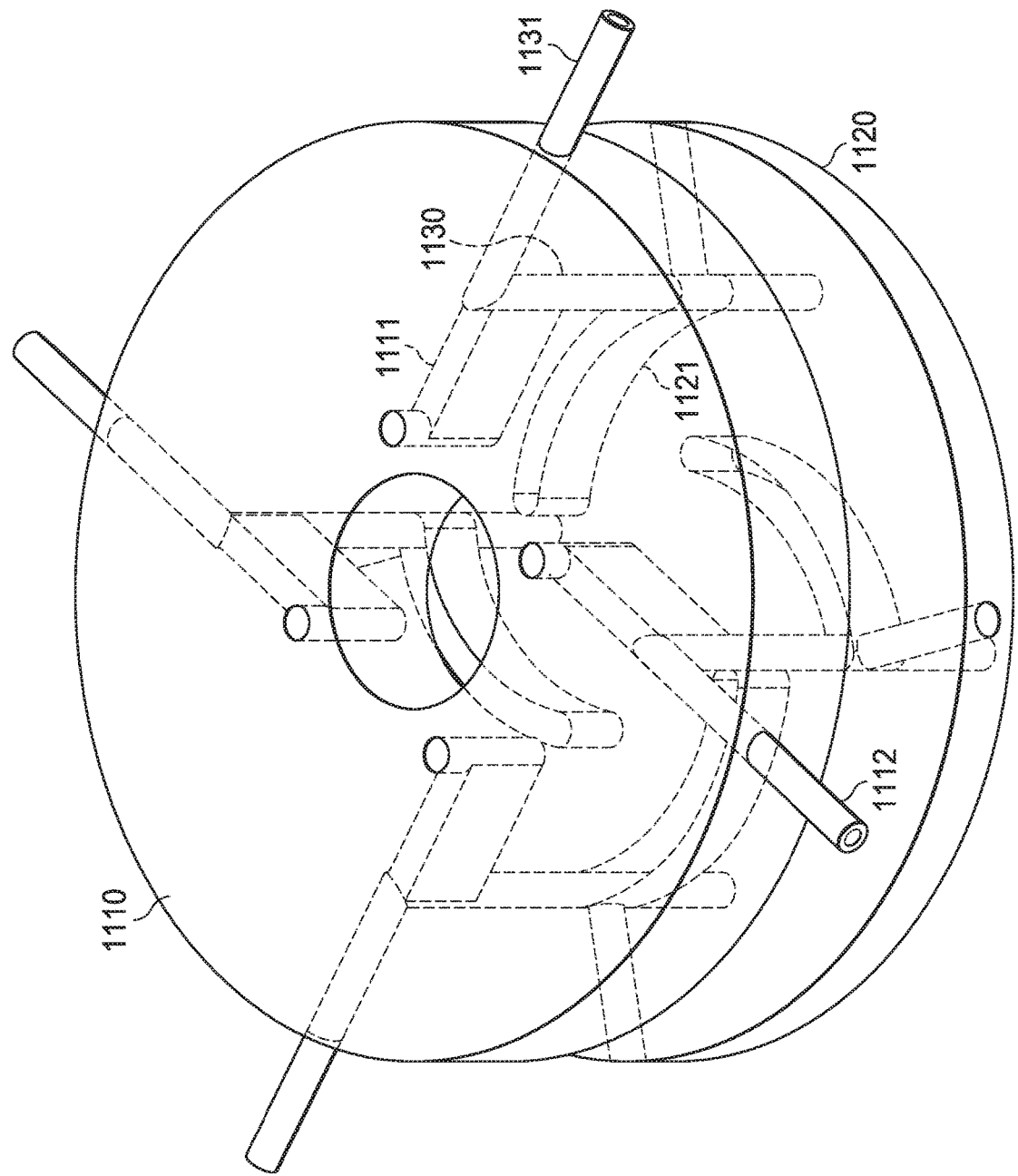
FIG. 12 is a sectional view of the cam-driven embodiment of FIG. 11 in a deployed position.

FIG. 11 is an isometric view of a cam-driven embodiment of a head of a rectal injection device (e.g., 200 of FIGS. 2 and 3) in a retracted position. Needles (one of which being referenced 1131) are captured in radial races (one of which being referenced 1111) of a first (upper in the view of FIG. 11) member 1110. Distal ends of axles (one of which being referenced 1130), associated with the needles (e.g., 1131) are captured in helical races 1121 of a second (lower in the view of FIG. 11) member 1120. As the first and second members 1110, 1120 rotate relative to one another in a first direction (the first member 1110 rotating clockwise relative to the second member 1120 in the embodiment of FIG. 11), the needles (e.g., 1131) are deployed from within the radial races (e.g., 1111) of the first member 1110. As the first and second members rotate relative to one another in a second, opposite direction (the first member 1110 rotating counter-clockwise relative to the second member 1120 in the embodiment of FIG. 11), e.g., 1131) are retracted into the radial races (e.g., 1111) of the first member 1110. The orientation of the helical races (e.g., 1121) determines the relative direction in which the first and second members 1110, 1120 are rotated relative to one another to deploy and retract the needles (e.g., 1131). The angle of the helical races (e.g., 1121) determines the rate at which the needles (e.g., 1131) are deployed and retracted relative to the motion of the first and second members 1110, 1120. FIG. 12 is a sectional view of the cam-driven embodiment of FIG. 11 with the needles in their deployed position.

Figure 13B:
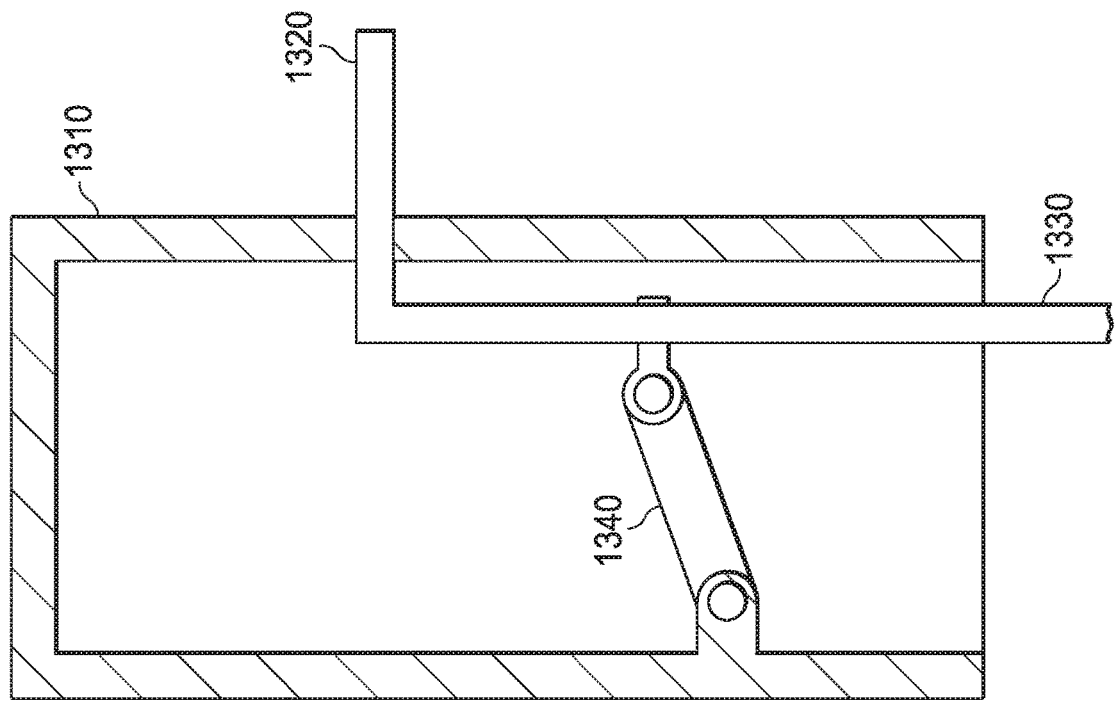
FIG. 13B is a sectional view of the arm-driven embodiment of FIG. 13A in a deployed position.
Figure 13A:
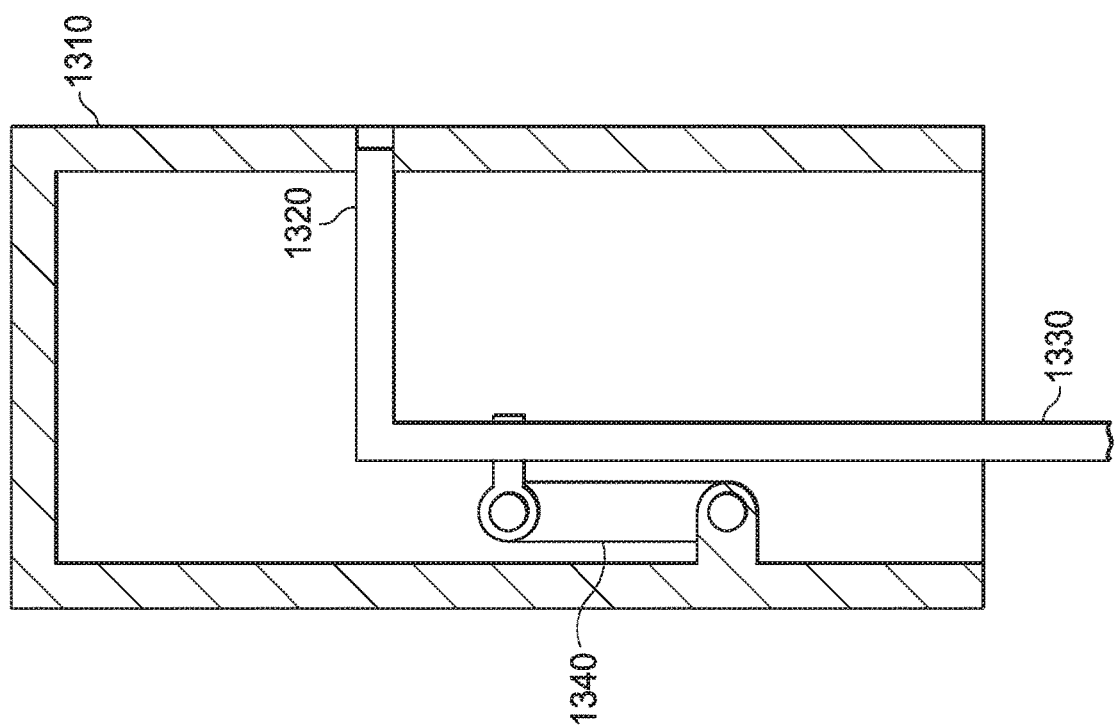
FIG. 13A is a sectional view of an arm-driven embodiment of a head of a rectal injection device in a retracted position.

FIG. 13A is a sectional view of an arm-driven embodiment of a head 1310 of a rectal injection device (e.g., 200 of FIGS. 2 and 3) in a retracted position. FIG. 13B is a sectional view of the arm-driven embodiment of FIG. 13A in a deployed position. Needles (only one of which being shown in FIGS. 13A and 13B and referenced as 1320) are provided with rigid shafts (only one of which being shown in FIGS. 13A and 13B and referenced as 1330) containing the passages and extending into the extension tube (not shown). The shafts (e.g., 1330) are coupled to arms (only one of which being shown in FIGS. 13A and 13B and referenced as 1340) that, when the shafts (e.g., 1330) are drawn downward as shown, the arms (e.g., 1340) cause the needles (e.g., 1320) to slide radially outward as shown.

FIGS. 6-13B do not show the passages that couple the needles to the reservoir(s). This is to keep FIGS. 6-13B relatively simple. Those skilled in the pertinent art will understand how to provide passages for liquid flow from the reservoir(s) to the roots of the needles, using, e.g., flexible plastic tubing. Also, the needles translate to deploy and retract in the embodiments of FIGS. 6-12. Now embodiments in which the needles rotate to deploy and retract will be described.

Figure 14A:
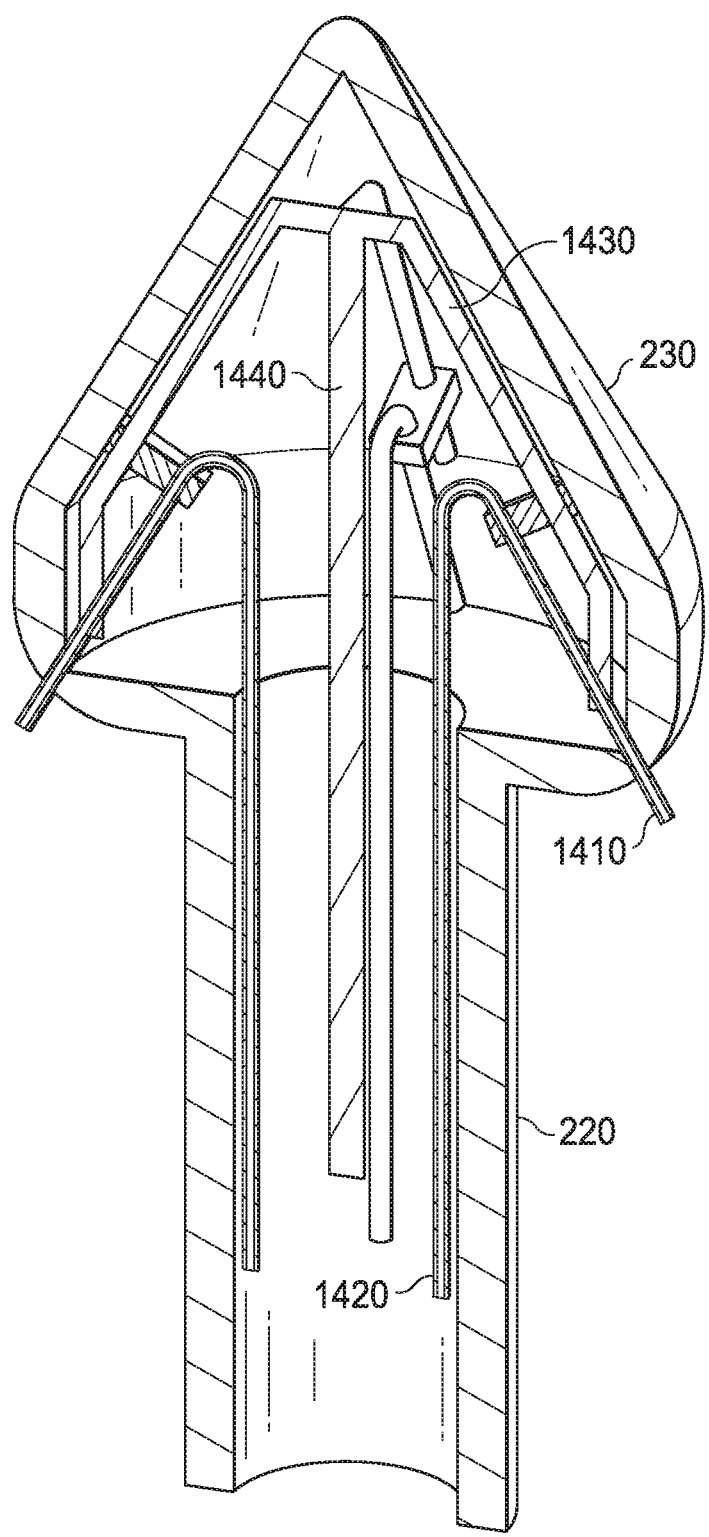
FIG. 14A is an isometric view of a rotating-needle embodiment of a head of a rectal injection device in a deployed position.
Figure 14B:
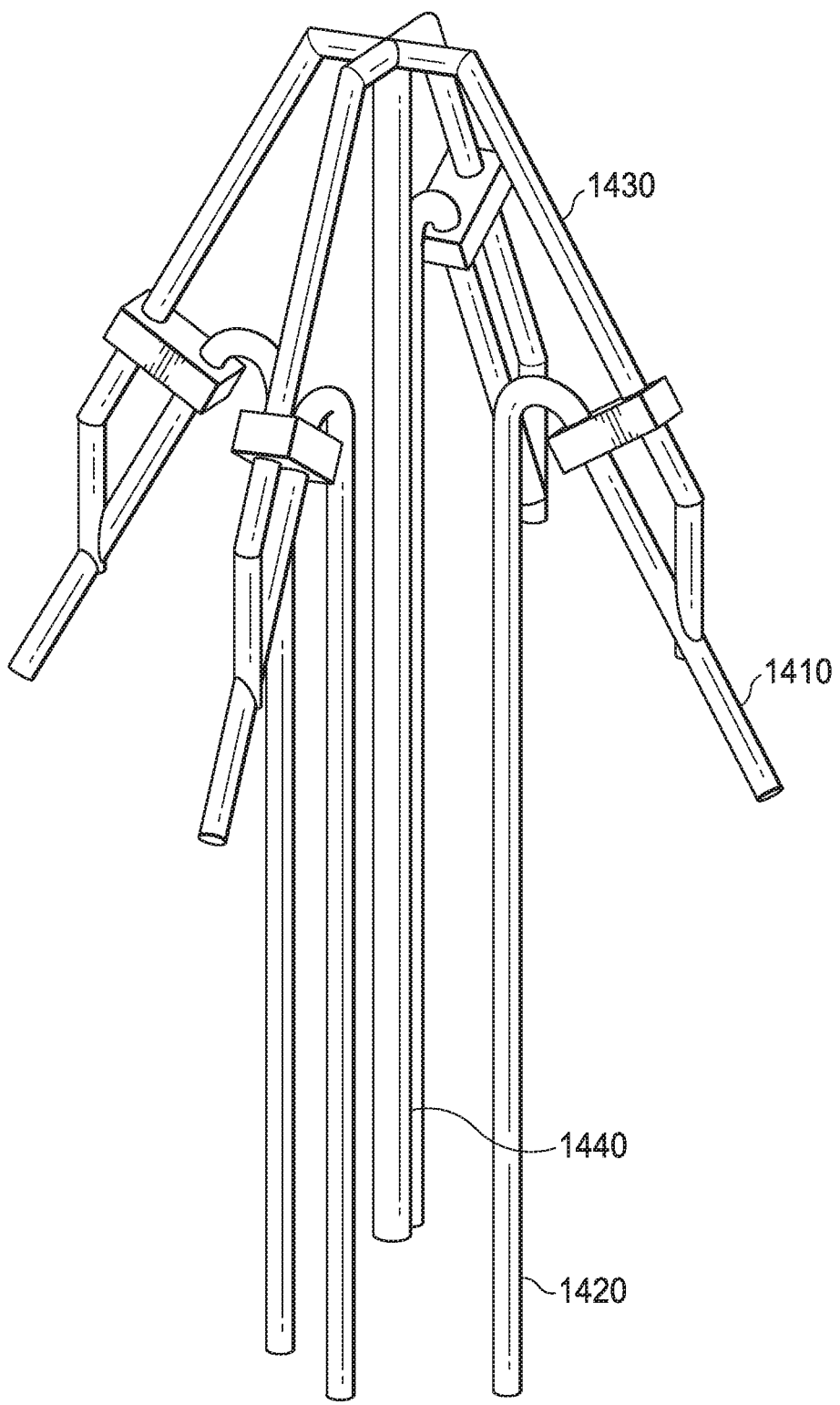
FIG. 14B is an isolated isometric vide of the rotating needle embodiment of FIG. 14A.

FIG. 14A is an isometric view of a rotating-needle embodiment of a head 230 of a rectal injection device (e.g., 200 of FIGS. 2 and 3) in a deployed position. Needles (one of which being referenced 1410) are coupled to passages (one of which being referenced 1420) that take the form of flexible shafts. A cage 1430 is coupled to the root (not referenced) of each of the needles (e.g., 1410). The needles (e.g., 1410) pass through apertures (not referenced) in the head 230 as shown. The cage 1430 and the needles (e.g., 1410) cooperate such that, as the cage 1430 is drawn back from the head 230 under the urging of a pullrod 1440, the needles (e.g., 1410) extend through the apertures and rotate outwardly to deploy. FIG. 14B is an isolated isometric vide of the rotating needle embodiment of FIG. 14A showing the needles (e.g., 1410), passages (e.g., 1420), cage 1430 and pullrod 1440 in isolation. When treatment is complete, the pullrod 1440 advances the cage 1430, and the needles (e.g., 1410) rotate inwardly as they retract back into the head 230.

Figure 15:
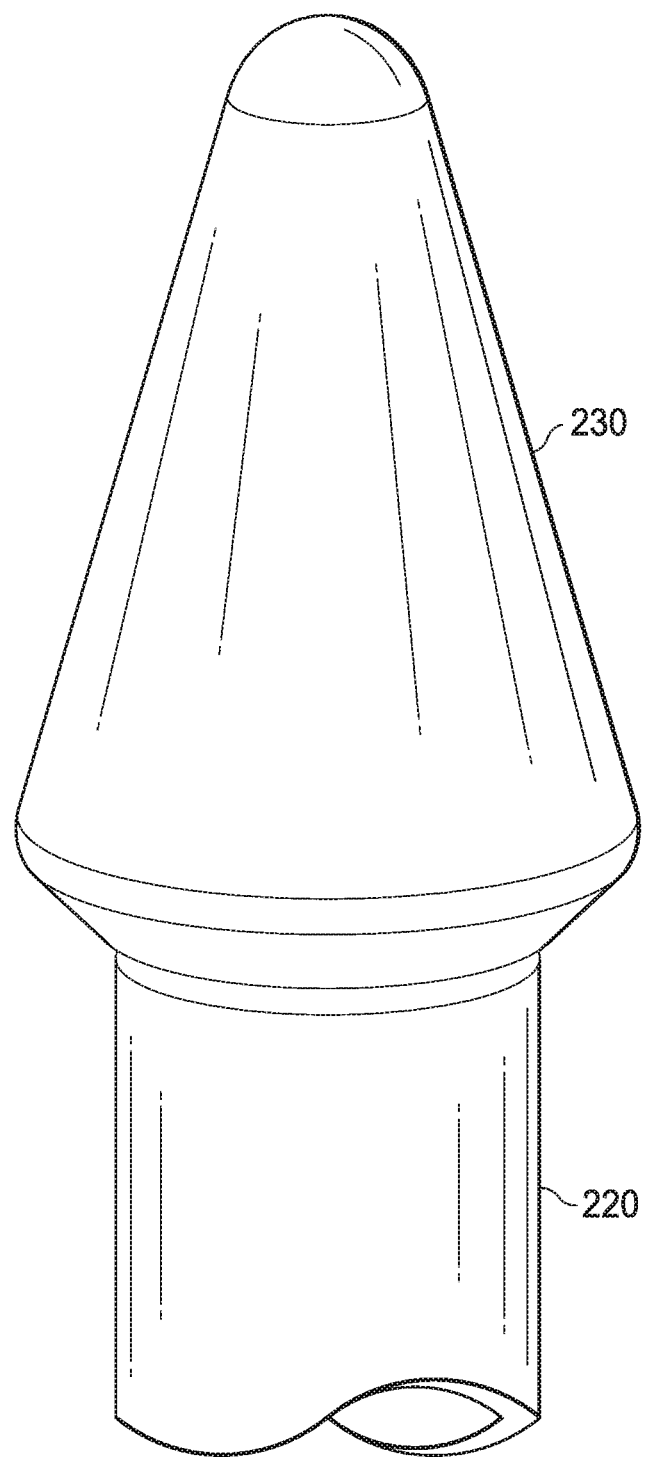
FIG. 15 is an isometric view of a conical-head embodiment of a head of a rectal injection device.

FIG. 15 is an isometric view of a conical-head embodiment of a head 230 of a rectal injection device (e.g., 200 of FIGS. 2 and 3). FIG. 15 is presented primarily for the purpose of showing a head 230 having a conical or frustoconical shape, together with the extension tube 220 that supports it.

FIG. 16 is an isometric view of a linear embodiment of a rectal injection device 200. The device 200 has an elongated handle 210, an extension tube 220 extending from the handle 210 and a head 230. The handle 210 is configured to be gripped by a human hand. The head 230 is configured to be inserted into a rectum of an animal, which may be a human, treat the rectum with an injection via a plurality of needles (not shown in FIG. 16) and be withdrawn from the rectum.

In the illustrated embodiment, the head 230 is bulbous. The extension tube 220 supports the head relative to the handle 210. A trigger 240 extends laterally from the handle and is configured to be moved to extend a plurality of needles (not shown) from within the head. In the illustrated embodiment, the trigger 240 is located beneath the handle 210 and configured to be translated away from the head 230 to extend the plurality of needles. An auto injection button 1610 also extends laterally from the handle and is configured to be depressed to cause a fluid, which may be a sclerosant, to flow from the device 200 through the plurality of needles. In the illustrated embodiment, the auto injection button 1610 is opposite the handle from the trigger, and therefore over the handle, as shown.

Three indicators are shown in the handle. From left to right, they are: a needle extension indicator 1620 configured to indicate whether or not the plurality of needles are deployed, an injection complete indicator 1630 configured to indicate whether or not the injection of fluid is complete and a syringe window 1640 configured to allow an outside observer (e.g., a person operating the device) to inspect an internal device syringe (not shown in FIG. 16) within the handle 210.

Figure 17:
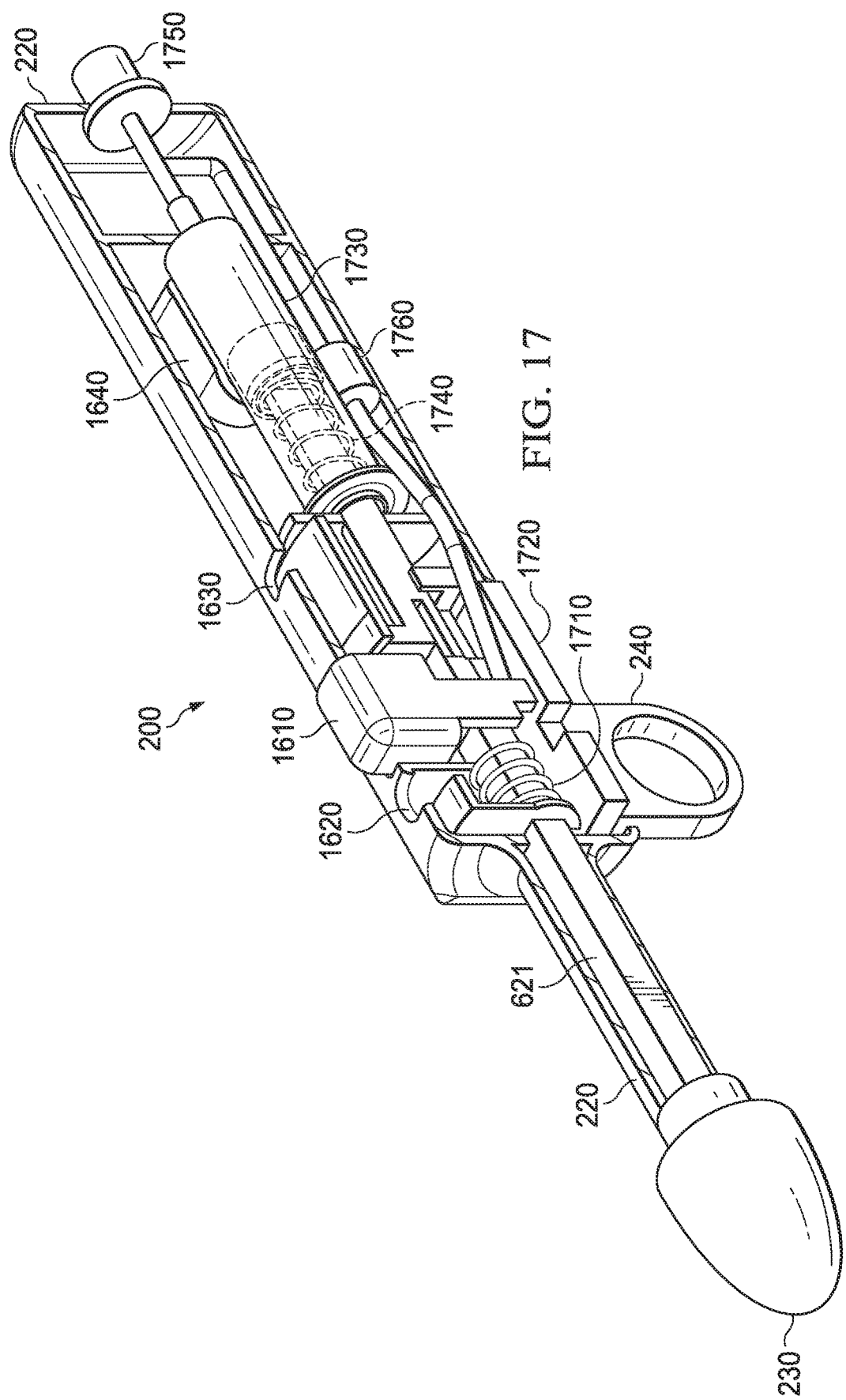
FIG. 17 is an isometric cutaway view of the linear embodiment of FIG. 16.

FIG. 17 is an isometric cutaway view of the linear embodiment of FIG. 16. FIG. 17 illustrates a pullrod 621 within the extension tube that actuates a plurality of needles (shown but not referenced in FIG. 17). An auto needle retract spring 1710 is configured to urge the pullrod 621 toward the head 230 and, accordingly, the plurality of needles toward a retracted position. FIG. 17 also shows how, in the illustrated embodiment, a flange 1720 associated with the trigger 240 is configured to interact with the auto injection button 1610 to prevent the auto injection button 1610 from being actuated until the trigger 240 has been pulled away from the head 230 a given distance.

FIG. 17 further shows an internal device syringe 1730 having an auto inject spring 1740 associated with a plunger (not referenced) thereof to allow the plunger to be activated automatically to cause fluid to flow out of the internal device syringe 1730 and through the plurality of needles when the auto injection button 1610 is depressed.

FIG. 17 also shows a fluid delivery system including a Luer activated fill port 1750, a check valve 1760 and tubing (unreferenced). The fluid delivery system is configured to allow fluid to be received from a fill syringe (not shown) and delivered to the internal device syringe 1730 and the needles. Those skilled in the pertinent art are aware of Luer activated fill ports. A Luer activated fill port is configured to deform in response to an applied pressure (typically from a fill syringe) to open and to reseal when the pressure is withdrawn. FIGS. 18A-C are isometric views of a Luer activated fill port (having an outer seal 1810 and an inner seal 1820) showing the Luer activated fill port in respective closed, partially open and fully open configurations in response to applied pressure from a fill syringe 1830, allowing fluid 1840 from the fill syringe 1830 to pass through the port.

FIGS. 19A and B are schematic views of two alternative priming systems. In the embodiment of FIG. 19A, the valve 1760 is a check valve having a cracking pressure greater than the pressure needed to fill the internal device syringe 1730. Thus, the fluid from the fill syringe 1830 enters through the Luer activated fill port 1750, first fills the internal device syringe 1730, then the check valve 1760 opens, allowing the fluid from the fill syringe 1 to fill the rest of the priming system and plurality of needles.

Figure 19B:
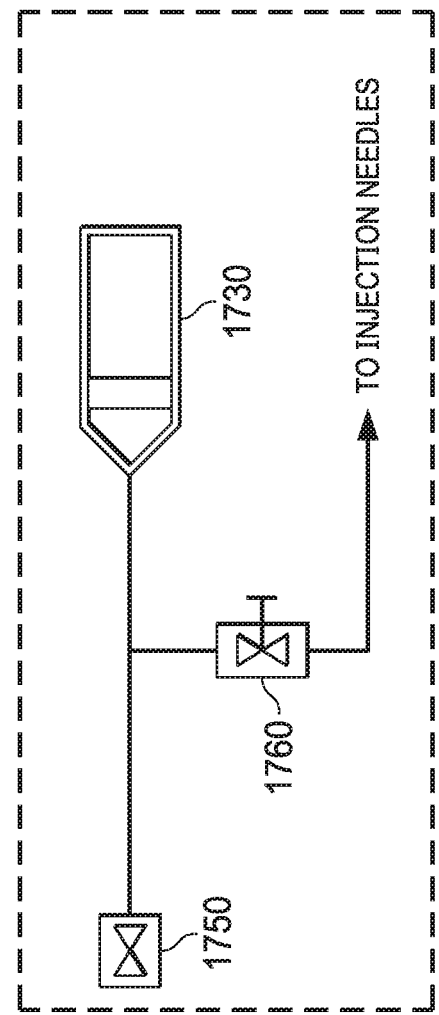

In the alternative embodiment of FIG. 19B, the valve is a manual valve 1760 configured to be manually closed to allow fluid from the fill syringe 1830 to fill the internal device syringe 1730, then manually opened to allow the fluid from the fill syringe 1830 to fill the rest of the priming system and plurality of needles.

Figure 20B:
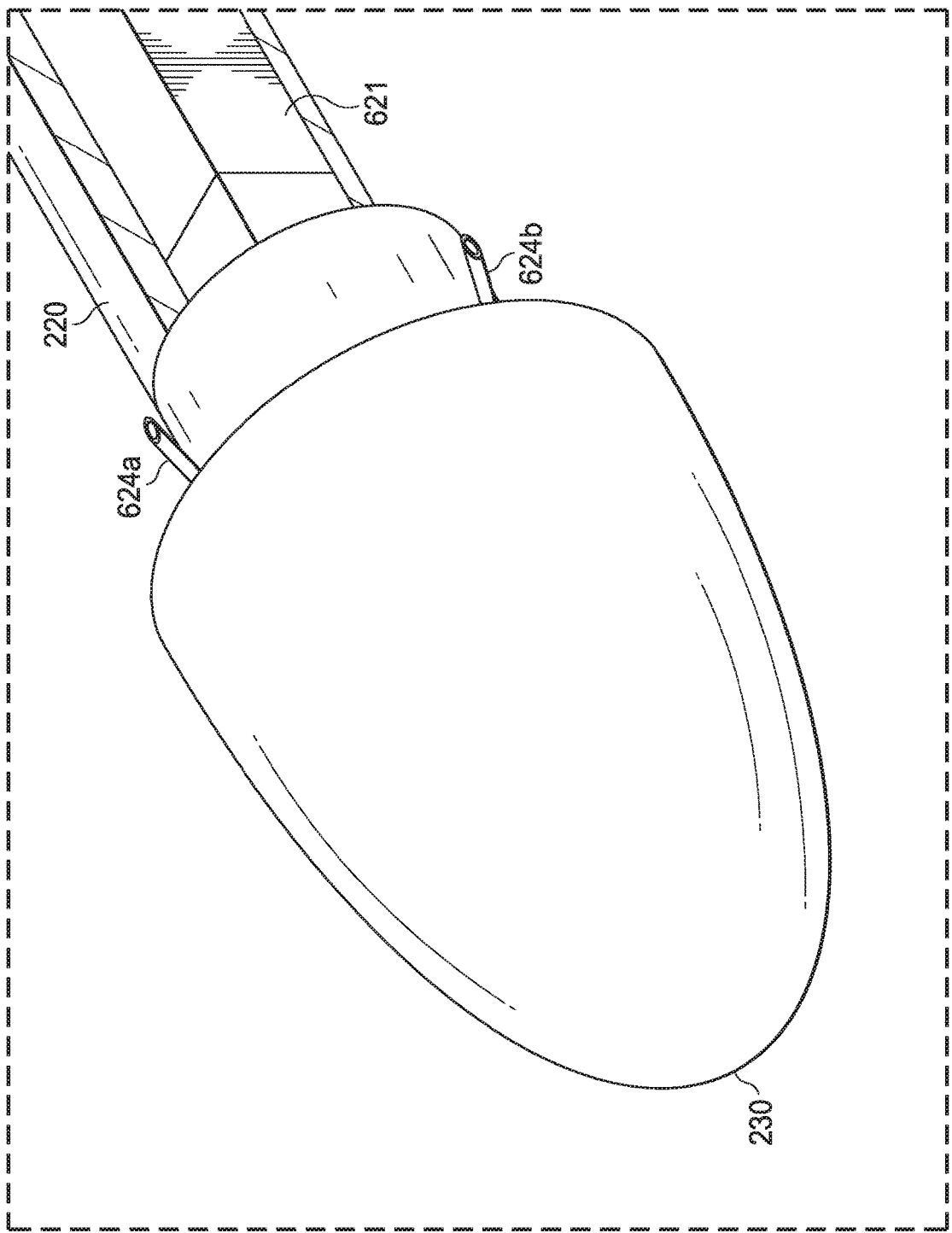

FIGS. 20A and B are respective isometric cutaway views of the linear rectal injection device 200 embodiment of FIG. 16 and a head 230 thereof. Once the device 200 has been primed with fluid, the device 200 is ready for treatment. Accordingly, the device 200 is intended to be inserted into the rectum of a patient (not shown) and pulled back slightly until the head 230 comes back to rest against the anal dentate thereof. The trigger 240 may then be pulled away from the head 230 as an arrow in FIG. 20A shows, causing the pullrod 621 to be pulled away from the head 230 and causing the plurality of needles 624a, 624b to extend from the head 230 into a region about the anal dentate as FIG. 20B shows. It will be noted that, in FIG. 20A, the trigger 240 has been pulled away fully, causing the needle extension indicator 1620 to indicate a full extension of the plurality of needles 624a, 624b and further causing a flange 1720 of the trigger 240 to align with the auto injection button 1610, unlocking the auto injection button 1610 for depression thereof.

Figure 21B:
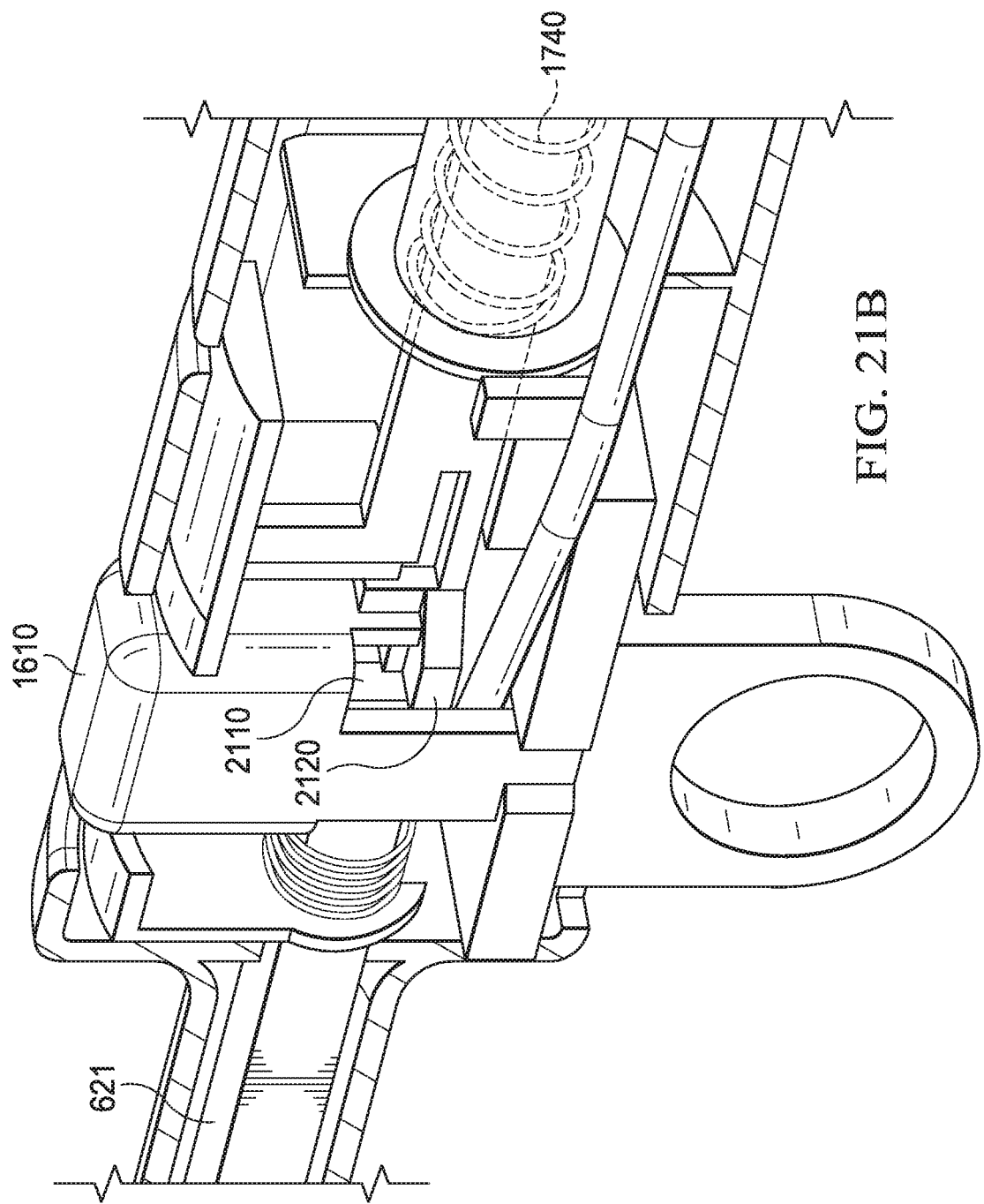

FIGS. 21A and B are respective isometric cutaway views of the linear rectal injection device 200 embodiment of FIG. 16 and a handle 210 thereof. FIG. 21A shows the auto injection button 1610 fully depressed, which, as FIG. 21B shows, has a feature 2110 that translates down to all an auto injection mechanism 2120 to become unlatched. This unlatching, in turn, releases the auto inject spring 1740 in the internal device syringe (not referenced) to relax, compressing the plunger within the internal device syringe and pressurizing the fluid therein. This pressurizing causes the fluid to be delivered to and through the plurality of needles.

FIGS. 22A and B are respective isometric cutaway views of the linear rectal injection device 200 embodiment of FIG. 16 and a handle 210 thereof. FIG. 22A shows the plunger (not referenced) close to or at the extreme end of its compressive travel, causing the injection complete indicator 1630 to indicate a full extension of the plurality of needles. FIG. 22B shows that, once the plunger is close to or at the extreme end of its compressive travel, the pullrod 621 is released, causing the plurality of needles to retract automatically under the urging of the auto needle retract spring, and causing the needle extension indicator 1620 to indicate that the needles have retracted. The head 230 of the rectal injection device 200 may then be withdrawn from the patient. A locking mechanism 2210 engages the pullrod 621 to prevent it from moving again, rendering the rectal injection device 200 a one-time-use device. In one embodiment, the device is disposable, and perhaps made of recyclable materials.

FIG. 23 is an isometric view of a pistol-handle embodiment of a rectal injection device 200. The pistol-handle embodiment is similar in many ways to the linear embodiment of FIG. 16. However, two differences may be noted in FIG. 23. First, there is no auto injection button. Second, the handle includes a pistol handle 210 protruding therefrom, e.g., at an acute angle.

FIG. 24 is an isometric cutaway view of the pistol-handle embodiment of FIG. 23. Further differences between this embodiment and that of FIG. 16 are now apparent. Primarily, the trigger is configured to rotate rather than translate, changing the way the trigger actuates the device.

FIGS. 25A-C are respective isometric cutaway views of the pistol-handle rectal injection device 200 embodiment of FIG. 23 and a head 230 and handle 210 thereof. After priming as with the linear embodiment of FIG. 16, the trigger 240 may be actuated. Actuation of the trigger 240 (as FIG. 25A shows) actuates a linkage 2410, forcing the pullrod 621 to translate away from the head 230 (as FIG. 25B shows) against the urging of the auto needle retract spring 2420 and causing the plurality of needles to extend from the head (as FIG. 25C shows). The needle extension indicator 1620 indicates the extension of the needles.

FIG. 26 is an isometric cutaway view of the pistol-handle embodiment of FIG. 23. Actuation of the trigger further forces, through a linkage 2610, the plunger of the internal device syringe 1730 to compress, causing the fluid in the internal device syringe 1730 to flow toward, through and out the plurality of needles.

FIGS. 27A and B are an isometric cutaway views of the pistol-handle rectal injection device 200 embodiment of FIG. 23 and a handle 210 thereof. Once the plunger is close to or at the extreme end of its compressive travel, the linkage 2410 holding the pullrod 621 in its position is released, causing the pullrod 621 to move back toward the head and the plurality of needles to retract automatically under the urging of the auto needle retract spring (not shown).

FIG. 28 is an isometric view of a T-handle embodiment of a rectal injection device. The T-handle embodiment is similar in many ways to the linear embodiment of FIG. 16. However, four differences may be noted in FIG. 28. First, there is no auto injection button (1610 of FIG. 16). Second, the trigger 240 is bifurcated into two symmetric trigger portions. Nonetheless, the trigger will be referred to in the singular. Third, a T-handle 210 protrudes from a rear portion of the device 200. Fourth, the Luer activated fill port 1750 is mounted on one side of the T-handle 210 instead of an end of the device 200.

FIG. 29 is an isometric cutaway view of the T-handle embodiment of FIG. 28. Like the embodiment of FIG. 16, the trigger 240 is configured to translate.

FIGS. 30A and B are respective isometric cutaway views of the T-handle embodiment of FIG. 28 and a head thereof. After priming as with the linear embodiment of FIG. 16, the trigger may be actuated. As the trigger is actuated, an O-ring 3010 associated with the pullrod 621 is configured to drag frictionally on the pullrod 621 to urge the pullrod 621 away from the head 230 and urge the plurality of needles into, and maintain the plurality of needles in, an deployed position while the fluid is being delivered through the plurality of needles. Actuation of the trigger 240 concurrently causes the plunger of the internal device syringe to compress, causing the fluid in the internal device syringe 1730 to flow toward, through and out the plurality of needles.

FIG. 31 is an isometric cutaway view of the T-handle embodiment of FIG. 23. FIG. 31 shows that the O-ring 3010 drags frictionally along the pullrod 621 to maintain the plurality of needles in an deployed position while the fluid is being delivered through the plurality of needles.

FIG. 32 is an isometric cutaway view of the T-handle embodiment of FIG. 23. Once the trigger 240 and plunger (not referenced) are close to or at the extreme end of their travel, the O-ring falls free from the pullrod 621, causing the pullrod 621 to move back toward the head 230 and the plurality of needles to retract automatically under the urging of the auto needle retract spring (not shown in FIG. 32).

FIGS. 33A-C are respective views of one embodiment of a rectal injection device head. FIG. 33A is an exploded view showing the needles (two of which being referenced 624*a*, 624*b*) embedded in needle carriers (one of which being referenced 3310), which allow the needles (e.g., 624*a*, 624*b*) to be captured in corresponding bearings 3320 at an end of the pullrod 621. A corresponding plurality of ramps on an insert 3330 of the head 230 maintain the orientation of the plurality of needles (e.g., 624*a*, 624*b*). FIGS. 33B and 33C show the plurality of needles (e.g., 624*a*, 624*b*) in retracted and deployed positions, respectively, while the pullrod 621 is translated from a more proximal position in FIG. 33B to a more distal position in FIG. 33C.

FIG. 34 is an isometric view of a linear embodiment of a rectal injection device 200. A few differences will be noted between the embodiment of FIG. 34 and the embodiment of FIG. 16. First, the handle 210 is curved to fit a human hand and hence more ergonomic. Second, a scale 3410 is printed on the extension tube 220 to assist the person operating the device 200 in determining the distance to which the device 200 has been inserted into a patient. It is also apparent that this embodiment of the device 200 has ornamental features not related to any of its functionality; it is attractive as well as useful. FIG. 35 is an isometric view of the linear embodiment of FIG. 34 from another angle.

FIG. 36 is an isometric cutaway view of the linear embodiment of FIG. 34. FIG. 36 is similar in many ways to FIG. 17 and will not be described further.

Figure 37B:
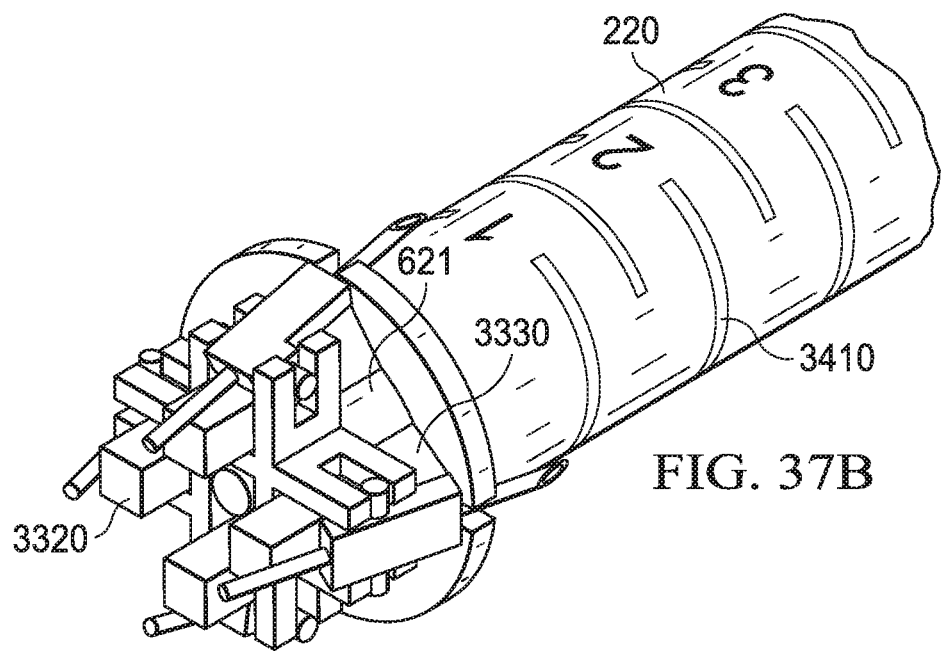

FIGS. 37A and B are cutaway views of a head of the rectal injection device of FIG. 34 with a cover of the head 230 removed to show the pullrod 621, the bearings 3320, the insert 3330 and the plurality of needles (unreferenced) in the head and the relationship between the extension tube and the head. FIG. 37A shows the needles in a retracted position, and FIG. 37B shows the needles in an deployed position.

FIG. 38 is a flow diagram of one embodiment of a method of using a rectal injection device. The method begins in a start step 3810. In a step 3820, the device is primed with a fluid, e.g., a sclerosant. In a step 3830, a head of the device is inserted into a rectum of an animal, e.g., a human. In a step 3840, the head is pulled back to cause the head to seat against the anal dentate of the rectum. In a step 3850, a plurality of needles of the device are deployed from the head so that they enter the rectum proximate the anal dentate. In a step 3860, the fluid is injected through the plurality of needles into the anal dentate. In a step 3870, the plurality of needles are retracted back into the head. In a step 3880, the head of the device is withdrawn from the rectum. The method ends in an end step 3890.

Those skilled in the art to which this application relates will appreciate that other and further additions, deletions, substitutions and modifications may be made to the described embodiments.

What is claimed is:

1. A method of operating a rectal injection device, comprising:
    inserting a head of said device into a rectum of a mammal;
    pulling back said head to cause said head to seat against an anal dentate of the rectum;
    deploying a plurality of needles of said device from said head so that they enter said rectum proximate said anal dentate; and
    injecting said fluid through the plurality of needles into said anal dentate.

2. The method as recited in claim 1 further comprising priming said device with a fluid.

3. The method as recited in claim 2 wherein said fluid is a sclerosant.

4. The method as recited in claim 1 wherein said mammal is a human.

5. The method as recited in claim 1 further comprising retracting said plurality of needles back into said head.

6. The method as recited in claim 1 further comprising withdrawing said head of said device from said rectum.

7. The method as recited in claim 1 further comprising employing a needle extension indicator to determine whether said plurality of needles are deployed.

8. The method as recited in claim 1 further comprising manually controlling a rate of said injecting.

9. The method as recited in claim 1 further comprising employing an injection complete indicator to determine whether said injecting has been fully carried out.

* * * * *